(12) United States Patent
Yarkoni et al.

(10) Patent No.: US 11,138,511 B2
(45) Date of Patent: Oct. 5, 2021

(54) PROBLEM SOLVING USING QUANTUM ANNEALER, USEFUL FOR EXAMPLE IN SEQUENCING, FOR INSTANCE NUCLEIC ACID SEQUENCING

(71) Applicant: D-Wave Systems Inc., Burnaby (CA)

(72) Inventors: Sheir Yarkoni, Vancouver (CA); Kelly T. R. Boothby, Coquitlam (CA); Adam Douglass, Vancouver (CA)

(73) Assignee: D-WAVE SYSTEMS INC., Burnaby (CA)

( * ) Notice: Subject to any disclaimer, the term of this patent is extended or adjusted under 35 U.S.C. 154(b) by 960 days.

(21) Appl. No.: 15/846,538

(22) Filed: Dec. 19, 2017

(65) Prior Publication Data

US 2018/0276550 A1    Sep. 27, 2018

Related U.S. Application Data

(60) Provisional application No. 62/446,157, filed on Jan. 13, 2017.

(51) Int. Cl.
| | |
|---|---|
| *G06N 5/04* | (2006.01) |
| *G06N 10/00* | (2019.01) |
| *G16B 30/00* | (2019.01) |
| *G16B 40/00* | (2019.01) |
| *G16B 50/00* | (2019.01) |
| *G06N 5/00* | (2006.01) |

(52) U.S. Cl.
CPC ............ *G06N 5/046* (2013.01); *G06N 5/003* (2013.01); *G06N 10/00* (2019.01); *G16B 30/00* (2019.02); *G16B 40/00* (2019.02); *G16B 50/00* (2019.02)

(58) Field of Classification Search
CPC .............................. G06N 5/046; G06N 10/00
See application file for complete search history.

(56) References Cited

U.S. PATENT DOCUMENTS

| | | | |
|---|---|---|---|
| 6,838,694 B2 | 1/2005 | Esteve et al. | |
| 7,135,701 B2 | 11/2006 | Amin et al. | |
| 7,418,283 B2 | 8/2008 | Amin | |
| 7,800,395 B2 | 9/2010 | Johnson et al. | |
| 7,898,282 B2 | 3/2011 | Harris et al. | |

(Continued)

OTHER PUBLICATIONS

Ibrahim, "Solving Unconstraint Assignment Problem by a Molecular-Based Computing Algorithm", IEEE, 2004 (Year: 2004).*

(Continued)

*Primary Examiner* — Ann J Lo
*Assistant Examiner* — Van C Mang
(74) *Attorney, Agent, or Firm* — Cozen O'Connor

(57) ABSTRACT

Quantum annealers as analog or quantum processors can find paths in problem graphs embedded in a hardware graph of the processor, for example finding valid paths, shortest paths or longest paths. A set of input, for example nucleic acid reads, can be used to set up a graph with edges between nodes denoting overlap (i.e., common base pairs) between the reads with constraints applied to perform sequence alignment or sequencing of a nucleic acid (e.g., DNA) strand or sequence, finding a solution that has a ground state energy. At least a portion of the described approaches can be applied to other problems, for instance resource allocations problems, e.g., job scheduling problems, traveling salesperson problems, and other NP-complete problems.

20 Claims, 7 Drawing Sheets

Specification includes a Sequence Listing.

(56) References Cited

U.S. PATENT DOCUMENTS

| | | | | |
|---|---|---|---|---|
| 8,244,662 | B2* | 8/2012 | Coury | G06T 11/206 706/46 |
| 8,655,828 | B2* | 2/2014 | Rose | G06K 9/6892 706/48 |
| 2005/0082519 | A1 | 4/2005 | Amin et al. | |
| 2005/0273306 | A1 | 12/2005 | Hilton et al. | |
| 2006/0147154 | A1 | 7/2006 | Thom et al. | |
| 2008/0052055 | A1 | 2/2008 | Rose et al. | |
| 2014/0250288 | A1* | 9/2014 | Roy | G06N 5/003 712/223 |

OTHER PUBLICATIONS

Teller, "Functional nucleic acid nanostructures and DNA machines", Science Direct, 2010 (Year: 2010).*

Choi, "Minor-embedding in adiabatic quantum computation: I. The parameter setting problem", 2008 (Year: 2008).*

Davide Venturelli "Quantum Annealing Implementation of Job-Shop Scheduling", 2015 (Year: 2015).*

Carsten Teller, "Functional nucleic acid nanostructures and DNA machines", Science Direct, 2010 (Year: 2010).*

Zuwairie Ibrahim, "Solving Unconstraint Assignment Problem by a Molecular-Based Computing Algorithm", IEEE, 2004 (Year: 2004).*

Vikcy Choi, "Minor-embedding in adiabatic quantum computation: I. The parameter setting problem" (Year: 2008).*

Gallop et al., "SQUIDs and their applications," *Journal of Physics E: Scientific Instruments* 9(6):417-429, 1976.

Kleiner et al., "Superconducting Quantum Interference Devices: State of the Art and Applications," *Proceedings of the IEEE* 92(10):1534-1548, 2004.

Makhlin et al., "Quantum-state engineering with Josephson-junction devices," *Reviews of Modern Physics* 73(2):357-400, 2001.

Nielsen et al., *Quantum Computation and Quantum Information*, Cambridge University Press, Cambridge, UK, 2000, pp. 343-345.

Venturelli et al., "Quantum Annealing Implementation of Job-Shop Scheduling," arXiv:1506.08479v1 [quant-ph] Jun. 29, 2015, 16 pages.

* cited by examiner

SEQUENCE LISTING

<160> NUMBER OF SEQ ID NOS: 20

<210> SEQ ID NO 1
<211> LENGTH: 32
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)...(32)
<223> OTHER INFORMATION: n = A,T,C or G

```
<400> SEQUENCE: 1
aggtnnnnnn nnnnatcgat tgagctctag cg                            32

<210> SEQ ID NO 2
<211> LENGTH: 32
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)...(32)
<223> OTHER INFORMATION: n = A,T,C or G

<400> SEQUENCE: 2
cgctagagct caatcgutnn nnnnnnnnac ct                            32

<210> SEQ ID NO 3
<211> LENGTH: 26
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)...(26)
<223> OTHER INFORMATION: n = A,T,C or G

<400> SEQUENCE: 3
ctagcgcata nnnnnnnnnn ggatct                                   26

<210> SEQ ID NO 4
<211> LENGTH: 26
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)...(26)
<223> OTHER INFORMATION: n = A,T,C or G

<400> SEQUENCE: 4
agatccnnnn nnnnnntatg cgctag                                   26

<210> SEQ ID NO 5
<211> LENGTH: 22
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)...(22)
<223> OTHER INFORMATION: n = A,T,C or G

<400> SEQUENCE: 5
tcaatgnnnn nnnnnngaag cg                                       22

<210> SEQ ID NO 6
<211> LENGTH: 22
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)...(22)
<223> OTHER INFORMATION: n = A,T,C or G
```

```
<400> SEQUENCE: 6
cgcttcnnnn nnnnnncatt ga                                              22

<210> SEQ ID NO 7
<211> LENGTH: 22
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)...(22)
<223> OTHER INFORMATION: n = A,T,C or G

<400> SEQUENCE: 7
gatcttnnnn nnnnnnttag tc                                              22

<210> SEQ ID NO 8
<211> LENGTH: 22
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)...(22)
<223> OTHER INFORMATION: n = A,T,C or G

<400> SEQUENCE: 8
gactaannnn nnnnnnaaga tc                                              22

<210> SEQ ID NO 9
<211> LENGTH: 21
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)...(21)
<223> OTHER INFORMATION: n = A,T,C or G

<400> SEQUENCE: 9
tagtctnnnn nnnnnngggc t                                               21

<210> SEQ ID NO 10
<211> LENGTH: 21
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)...(21)
<223> OTHER INFORMATION: n = A,T,C or G

<400> SEQUENCE: 10
agcccnnnnn nnnnnagact a                                               21

<210> SEQ ID NO 11
<211> LENGTH: 32
<212> TYPE: RNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)...(32)
```

<223> OTHER INFORMATION: n = A,T,C or G

<400> SEQUENCE: 11
aggunnnnnn nnnnaucgau ugagcucuag cg               32

<210> SEQ ID NO 12
<211> LENGTH: 32
<212> TYPE: RNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)...(32)
<223> OTHER INFORMATION: n = A,T,C or G

<400> SEQUENCE: 12
cgcuagagcu caaucguunn nnnnnnnnac cu               32

<210> SEQ ID NO 13
<211> LENGTH: 26
<212> TYPE: RNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)...(26)
<223> OTHER INFORMATION: n = A,T,C or G

<400> SEQUENCE: 13
cuagcgcaua nnnnnnnnnn ggaucu               26

<210> SEQ ID NO 14
<211> LENGTH: 26
<212> TYPE: RNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)...(26)
<223> OTHER INFORMATION: n = A,T,C or G

<400> SEQUENCE: 14
agauccnnnn nnnnnnuaug cgcuag               26

<210> SEQ ID NO 15
<211> LENGTH: 22
<212> TYPE: RNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)...(22)
<223> OTHER INFORMATION: n = A,T,C or G

<400> SEQUENCE: 15
ucaaugnnnn nnnnnngaag cg               22

<210> SEQ ID NO 16
<211> LENGTH: 22
<212> TYPE: RNA
<213> ORGANISM: Artificial Sequence
<220> FEATURE:
<223> OTHER INFORMATION: Synthetic sequence
<220> FEATURE:
<221> NAME/KEY: misc_feature

```
<222> LOCATION: (1)...(22)
<223> OTHER INFORMATION: n = A,T,C or G

<400> SEQUENCE: 16
cgcuucnnnn nnnnnncauu ga                                              22

<210> SEQ ID NO 17
<211> LENGTH: 22
<212> TYPE: RNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)...(22)
<223> OTHER INFORMATION: n = A,T,C or G

<400> SEQUENCE: 17
gaucuunnnn nnnnnnuuag uc                                              22

<210> SEQ ID NO 18
<211> LENGTH: 22
<212> TYPE: RNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)...(22)
<223> OTHER INFORMATION: n = A,T,C or G

<400> SEQUENCE: 18
gacuaannnn nnnnnnaaga uc                                              22

<210> SEQ ID NO 19
<211> LENGTH: 21
<212> TYPE: RNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)...(21)
<223> OTHER INFORMATION: n = A,T,C or G

<400> SEQUENCE: 19
uagucunnnn nnnnnngggc u                                               21

<210> SEQ ID NO 20
<211> LENGTH: 21
<212> TYPE: RNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)...(21)
<223> OTHER INFORMATION: n = A,T,C or G

<400> SEQUENCE: 20
agcccnnnnn nnnnnagacu a                                               21
```

PROBLEM SOLVING USING QUANTUM ANNEALER, USEFUL FOR EXAMPLE IN SEQUENCING, FOR INSTANCE NUCLEIC ACID SEQUENCING

STATEMENT REGARDING SEQUENCE LISTING

The Sequence Listing associated with this application is provided in text format in lieu of a paper copy, and is hereby incorporated by reference into the specification. The name of the text file containing the Sequence Listing is 240105_584_SEQUENCE_LISTING.txt. The text file is 5.4 KB, was created on Jun. 4, 2018, and is being submitted electronically via EFS-Web.

TECHNICAL FIELD

The present methods, system and apparatus relate to problem solvers that employ quantum annealers, which can be used to find paths (e.g., valid paths, shortest path, longest path) in a graph, and which can be used to perform sequence alignment or sequencing for example DNA sequencing.

BACKGROUND

Description of the Related Art

Nucleic Acid Sequencing

Nucleic Acid (e.g., DNA, RNA) sequencing has transformed the fields of medicine and genetics research. The costs associated with Nucleic Acid sequencing have decreased in recent years. However, Nucleic Acid sequencing still faces many computational impediments. For example, the problem of DNA sequence alignment hinders many research experiments.

Current generation sequencers ("next-gen" sequencers) break up Nucleic Acid strands into small segments, thus returning may small subsequences of the original Nucleic Acid strand or sequence. These subsequences are commonly referred to as reads. While each read in itself is fairly accurate, it is still a computationally complex problem to reconstruct the original Nucleic Acid strand or sequence from the various reads or subsequences. Depending on the size or "length" of the Nucleic Acid sequence, it can take days, weeks or even months to reconstruct the original Nucleic Acid strand or sequence using conventional approaches.

Faster approaches are, of course, desirable.

Quantum Devices

Quantum devices are structures in which quantum mechanical effects are observable. Quantum devices include circuits in which current transport is dominated by quantum mechanical effects. Such devices include spintronics, where electronic spin is used as a resource, and superconducting circuits. Both spin and superconductivity are quantum mechanical phenomena. Quantum devices can be used for measurement instruments, in computing machinery, and the like.

Quantum Computation

Quantum computation and quantum information processing are active areas of research and define classes of vendible products. A quantum computer is a system that makes direct use of at least one quantum-mechanical phenomenon, such as, superposition, tunneling, and entanglement, to perform operations on data. The elements of a quantum computer are not binary digits (bits) but typically are quantum binary digits or qubits.

Qubits can be used as fundamental units of information for a quantum computer. Qubits can refer to at least two distinct quantities; a qubit can refer to the actual physical device in which information is stored, and it can also refer to the unit of information itself, abstracted away from its physical device.

Qubits generalize the concept of a classical digital bit. A classical information storage device can encode two discrete states, typically labeled "0" and "1." Physically these two discrete states are represented by two different and distinguishable physical states of the classical information storage device, such as direction or magnitude of magnetic field, current or voltage, where the quantity encoding the bit state behaves according to the laws of classical physics. A qubit also contains two discrete physical states, which can also be labeled "0" and "1." Physically these two discrete states are represented by two different and distinguishable physical states of the quantum information storage device, such as direction or magnitude of magnetic field, current or voltage, where the quantity encoding the bit state behaves according to the laws of quantum physics. If the physical quantity that stores these states behaves quantum mechanically, the device can additionally be placed in a superposition of 0 and 1. That is, the qubit can exist in both a "0" and "1" state at the same time, and so can perform a computation on both states simultaneously. In general, N qubits can be in a superposition of $2^N$ states. Quantum algorithms make use of the superposition property to speed up some computations.

In standard notation, the basis states of a qubit are referred to as the $|0\rangle$ and $|1\rangle$ states. During quantum computation, the state of a qubit, in general, is a superposition of basis states so that the qubit has a nonzero probability of occupying the $|0\rangle$ basis state and a simultaneous nonzero probability of occupying the $|1\rangle$ basis state. Mathematically, a superposition of basis states means that the overall state of the qubit, which is denoted $|\Psi\rangle$, has the form $|\Psi\rangle = a|0\rangle + b|1\rangle$, where a and b are coefficients corresponding to the probabilities $|a|^2$ and $|b|^2$, respectively. The coefficients a and b each have real and imaginary components. The quantum nature of a qubit is largely derived from its ability to exist in a coherent superposition of basis states. A qubit will retain this ability to exist as a coherent superposition of basis states when the qubit is sufficiently isolated from sources of decoherence.

To complete a computation using a qubit, the state of the qubit is measured (i.e., read out). Typically, when a measurement of the qubit is performed, the quantum nature of the qubit is temporarily lost and the superposition of basis states collapses to either the $|0\rangle$ basis state or the $|1\rangle$ basis state and, thus, regains its similarity to a conventional bit. The actual state of the qubit after it has collapsed depends on the probabilities $|a|^2$ and $|b|^2$ immediately prior to the readout operation.

There are several types of quantum computers. An early proposal from Feynman in 1981 included creating artificial lattices of spins. More complicated proposals followed including a quantum circuit model where logical gates are applied to qubits in a time ordered way. In 2000, a model of computing was introduced for solving satisfiability problems; based on the adiabatic theorem, this model is called adiabatic quantum computing. This model is believed useful for solving hard optimization problems and potentially other problems. Further details on adiabatic quantum computing systems, methods, and apparatus are described in, for example, U.S. Pat. Nos. 7,135,701 and 7,418,283.

Superconducting qubits are a type of superconducting device that can be included in a superconducting integrated circuit. Superconducting qubits can be separated into several categories depending on the physical property used to encode information. For example, they may be separated into charge, flux and phase devices, as discussed in, for example, Makhlin et al., 2001, *Reviews of Modern Physics* 73, pp. 357-400. Charge devices store and manipulate information in the charge states of the device, where elementary charges consist of pairs of electrons called Cooper pairs. A Cooper pair has a charge of 2e and consists of two electrons bound together by, for example, a phonon interaction. See, e.g., Nielsen and Chuang, *Quantum Computation and Quantum Information*, Cambridge University Press, Cambridge (2000), pp. 343-345. Flux devices store information in a variable related to the magnetic flux through some part of the device. Phase devices store information in a variable related to the difference in superconducting phase between two regions of the phase device. Recently, hybrid devices using two or more of charge, flux and phase degrees of freedom have been developed. See, e.g., U.S. Pat. No. 6,838,694 and U.S. Patent Publication No. 2005-0082519, which are hereby incorporated by reference in their entireties.

Quantum Annealing

Quantum annealing is a computation method that may be used to find a low-energy state, typically the ground state, of a system. Similar in some respects to classical simulated annealing, the approach relies on the underlying principle that natural systems tend towards lower energy states because lower energy states are more stable. However, while classical annealing uses classical thermal fluctuations to guide a system to a low-energy state and, ideally, its global energy minimum, quantum annealing may use quantum effects, such as quantum tunneling, as a source of delocalization to reach a global energy minimum more accurately and/or more quickly than classical annealing. In quantum annealing, thermal effects and other noise may be present. The final low-energy state may not be the global energy minimum.

Adiabatic quantum computation may be considered a special case of quantum annealing for which the system, ideally, begins and remains in its ground state throughout an adiabatic evolution. Thus, those of skill in the art will appreciate that quantum annealing systems and methods may generally be implemented on an adiabatic quantum computer. Throughout this specification and the appended claims, any reference to quantum annealing is intended to encompass adiabatic quantum computation unless the context requires otherwise.

Quantum annealing uses quantum mechanics as a source of delocalization, sometimes called disorder, during the annealing process.

The foregoing examples of the related art and limitations related thereto are intended to be illustrative and not exclusive. Other limitations of the related art will become apparent to those of skill in the art upon a reading of the specification and a study of the drawings.

BRIEF SUMMARY

A method of problem solving via a quantum annealer may be summarized as including for a set of a number $N_{READS}$ of nucleic acid reads r, for each nucleic acid read $r_i$ in the set of nucleic acid reads r, finding all other nucleic acid reads $r_j$ in the set of nucleic acid reads that have at least a defined number of base pairs at one end of the other nucleic acid read $r_j$ in common with the defined number of base pairs at one end of the nucleic acid read $r_i$; forming a problem graph having a number of rows equal to a defined sequence length $l_{SEQ}$, each row having a total number of nodes equal to the defined number of base pairs, and where for each pair of nucleic acid reads $r_{i,j}$ that have the defined number of base pairs in common, the problem graph has a respective edge that extends from a node $r_i$ in one row to a node $r_j$ in a next row in the problem graph; for each column of the problem graph, asserting a first constraint that either one node or zero nodes in the column are in a ground state; for each row of the problem graph, asserting a second constraint that exactly one node in the row is in the ground state; causing the problem graph to be embedded in a hardware graph of the quantum annealer along with the first and the second constraints; and receiving a result from the quantum annealer after at least one evolution with the problem graph embedded in the hardware graph of the quantum annealer along with the first and the second constraints.

Forming a problem graph may include for each row of the problem graph except a last one of the rows in the problem graph, iterating over all pairs of nucleic acid reads r that have the defined number of base pairs in common, and forming an edge relationship between a node $r_i$ in one row to a node $r_j$ in a next row in the problem graph. Finding all other nucleic acid reads $r_j$ in the set of nucleic acid reads that have at least a defined number of base pairs at one end of the other nucleic acid read $r_j$ in common with the defined number of base pairs at one end of the nucleic acid read $r_i$; may include finding all other nucleic acid reads $r_j$ in the set of nucleic acid reads that have at least a defined number of base pairs at a first end of the other nucleic acid read $r_j$ in common with the defined number of base pairs at a second end of the nucleic acid read $r_i$, the second end opposite the first end. Causing the problem graph to be embedded in a hardware graph of the quantum annealer along with the first and the second constraints may include embedding the problem graph with the first and the second constraints in the hardware graph of an analog processor. Causing the problem graph to be embedded in a hardware graph of the quantum annealer along with the first and the second constraints may include embedding the problem graph with the first and the second constraints in the hardware graph of a quantum processor. The quantum annealer may be a quantum processor that includes a plurality of quantum devices spatially arranged in an interconnected topology and a plurality of coupling devices between pairs of quantum devices, and wherein causing the problem graph to be embedded in a hardware graph of the quantum annealer along with the first and the second constraints may include programming at least a portion of the quantum devices and the coupling devices to set an energy function of the quantum processor.

The method may further include initializing the quantum processor to an initial state; and evolving the quantum processor from the initial state to a final state. Evolving the analog processor from the initial state to a final state may occur a plurality of times via at least one of adiabatic evolution, quasi-adiabatic evolution, annealing by temperature, annealing by magnetic field, and annealing of barrier height, until a ground state energy is obtained.

The method may further include determining whether a ground state energy was obtained at the end of the evolution. Receiving a result from the quantum annealer may include receiving a result that represents an ordered sequence of nucleotides over a strand of deoxyribose nucleic acid (DNA) or ribose nucleic acid (RNA) of the defined sequence length $l_{SEQ}$.

A system to problem solve may be summarized as including at least one processor circuit; and at least one processor-readable medium that stores at least one of processor-executable instructions or data which, when executed by the at least one processor causes the at least one processor to: form a problem graph having a number of rows equal to a defined sequence length l, each row having a total number of nodes equal to a defined number of base pairs, and where for each pair of DNA reads $r_{i,j}$ that have the defined number of base pairs in common, the problem graph has a respective edge that extends from a node $r_i$ in one row to a node $r_j$ in a next row in the problem graph; for each column of the problem graph, assert a first constraint that either one node or zero nodes in the column are in a ground state; for each row of the problem graph, assert a second constraint that exactly one node in the row is in the ground state; cause the problem graph to be embedded in a hardware graph of the quantum annealer along with the first and the second constraints; and receive a result from the quantum annealer after at least one evolution with the problem graph embedded in the hardware graph of the quantum annealer along with the first and the second constraints. The system may be operable to execute any of the methods described herein.

A method of finding a path in a graph via a quantum annealer may be summarized as including forming a problem graph having a number of rows equal to a defined sequence length $l_{SEQ}$, each row having a total number of nodes equal to the defined number of sequential values, and where for each pair of subsequences $r_{i,j}$ that have the defined number of sequential values in common, the problem graph has a respective edge that extends from a node $r_i$ in one row to a node $r_j$ in a next row in the problem graph; for each column of the problem graph, asserting a first constraint that either one node or zero nodes in the column are in a ground state; for each row of the problem graph, asserting a second constraint that exactly one node in the row is in the ground state; causing the problem graph to be embedded in a hardware graph of the quantum annealer along with the first and the second constraints; and receiving a result from the quantum annealer after at least one evolution with the problem graph embedded in the hardware graph of the quantum annealer along with the first and the second constraints.

Forming a problem graph may include for each row of the problem graph, except a last one of the rows in the problem graph, iterating over all pairs of pair of subsequences $r_{i,j}$ that have the defined number of sequential values in common, and forming an edge relationship between a node $r_i$ in one row to a node $r_j$ in a next row in the problem graph. Causing the problem graph to be embedded in a hardware graph of the quantum annealer along with the first and the second constraints may include embedding the problem graph with the first and the second constraints in the hardware graph of an analog processor. Causing the problem graph to be embedded in a hardware graph of the quantum annealer along with the first and the second constraints may include embedding the problem graph with the first and the second constraints in the hardware graph of a quantum processor. The quantum annealer may be a quantum processor that includes a plurality of quantum devices spatially arranged in an interconnected topology and a plurality of coupling devices between pairs of quantum devices, and wherein causing the problem graph to be embedded in a hardware graph of the quantum annealer along with the first and the second constraints may include programming at least a portion of the quantum devices and the coupling devices to set an energy function of the quantum processor.

The method may further include initializing the quantum processor to an initial state; and evolving the quantum processor from the initial state to a final state. Evolving the analog processor from the initial state to a final state may occur a plurality of times via at least one of adiabatic evolution, quasi-adiabatic evolution, annealing by temperature, annealing by magnetic field, and annealing of barrier height, until a ground state energy is obtained.

The method may further include determining whether a ground state energy was obtained at the end of the evolution. Forming a problem graph may include forming the problem graph having a number of rows equal to a defined sequence length $l_{SEQ}$ of a strand of nucleic acid, each row having a total number of nodes equal to the defined number of sequential base pairs, and where for each pair of subsequences $r_{i,j}$ that have the defined number of sequential base pairs in common, the problem graph may have a respective edge that extends from the node $r_i$ in one row to the node $r_j$ in the next row in the problem graph.

The method may further include finding all other nucleic acid reads $r_j$ in the set of nucleic acid reads that have at least a defined number of base pairs at one end of the other nucleic acid read $r_j$ in common with the defined number of base pairs at one end of the nucleic acid read $r_i$. Finding all other nucleic acid reads $r_j$ in the set of nucleic acid reads that have at least a defined number of base pairs at one end of the other nucleic acid read $r_j$ in common with the defined number of base pairs at one end of the nucleic acid read $r_i$ may include finding all other nucleic acid reads $r_j$ in the set of nucleic acid reads that have at least a defined number of base pairs at a first end of the other nucleic acid read $r_j$ in common with the defined number of base pairs at a second end of the nucleic acid read $r_i$, the second end opposite the first end.

A system to problem solve may be summarized as including at least one processor circuit; and at least one processor-readable medium that stores at least one of processor-executable instructions or data which, when executed by the at least one processor causes the at least one processor to: form a problem graph having a number of rows equal to a defined sequence length $l_{SEQ}$, each row having a total number of nodes equal to the defined number of sequential values, where for each pair of subsequences $r_{i,j}$ that have the defined number of sequential values in common, the problem graph has a respective edge that extends from a node $r_i$ in one row to a node $r_j$ in a next row in the problem graph; for each column of the problem graph, assert a first constraint that either one node or zero nodes in the column are in a ground state; for each row of the problem graph, assert a second constraint that exactly one node in the row is in the ground state; cause the problem graph to be embedded in a hardware graph of the quantum annealer along with the first and the second constraints; and receive a result from the quantum annealer after at least one evolution with the problem graph embedded in the hardware graph of the quantum annealer along with the first and the second constraints.

The system may be operable to execute any of the methods described herein.

BRIEF DESCRIPTION OF THE SEVERAL VIEWS OF THE DRAWINGS

In the Figures, identical reference numbers identify similar elements or acts. The sizes and relative positions of elements in the figures are not necessarily drawn to scale. For example, the shapes of various elements and angles are not necessarily drawn to scale, and some of these elements are arbitrarily enlarged and positioned to improve legibility. Further, the particular shapes of the elements as drawn are not necessarily intended to convey any information regarding the actual shape of the particular elements and have been solely selected for ease of recognition in the figures. Furthermore, while the figures may show specific layouts, one skilled in the art will appreciate that variations in design, layout, and fabrication are possible and the shown layouts are not to be construed as limiting the geometry of the present systems, methods and apparatus.

DETAILED DESCRIPTION

In the following description, certain specific details are set forth in order to provide a thorough understanding of various disclosed implementations. However, one skilled in the relevant art will recognize that implementations may be practiced without one or more of these specific details, or with other methods, components, materials, etc. In other instances, well-known structures associated with computer systems, server computers, and/or communications networks and associated hardware components or circuitry have not been shown or described in detail to avoid unnecessarily obscuring descriptions of the implementations.

Unless the context requires otherwise, throughout the specification and claims that follow, the word "comprising" is synonymous with "including," and is inclusive or open-ended (i.e., does not exclude additional, unrecited elements or method acts).

Reference throughout this specification to "one implementation" or "an implementation" means that a particular feature, structure or characteristic described in connection with the implementation is included in at least one implementation. Thus, the appearances of the phrases "in one implementation" or "in an implementation" in various places throughout this specification are not necessarily all referring to the same implementation. Furthermore, the particular features, structures, or characteristics may be combined in any suitable manner in one or more implementations.

As used in this specification and the appended claims, the singular forms "a," "an," and "the" include plural referents unless the context clearly dictates otherwise. It should also be noted that the term "or" is generally employed in its sense including "and/or" unless the context clearly dictates otherwise.

The headings and Abstract of the Disclosure provided herein are for convenience only and do not interpret the scope or meaning of the implementations.

Figure 1:
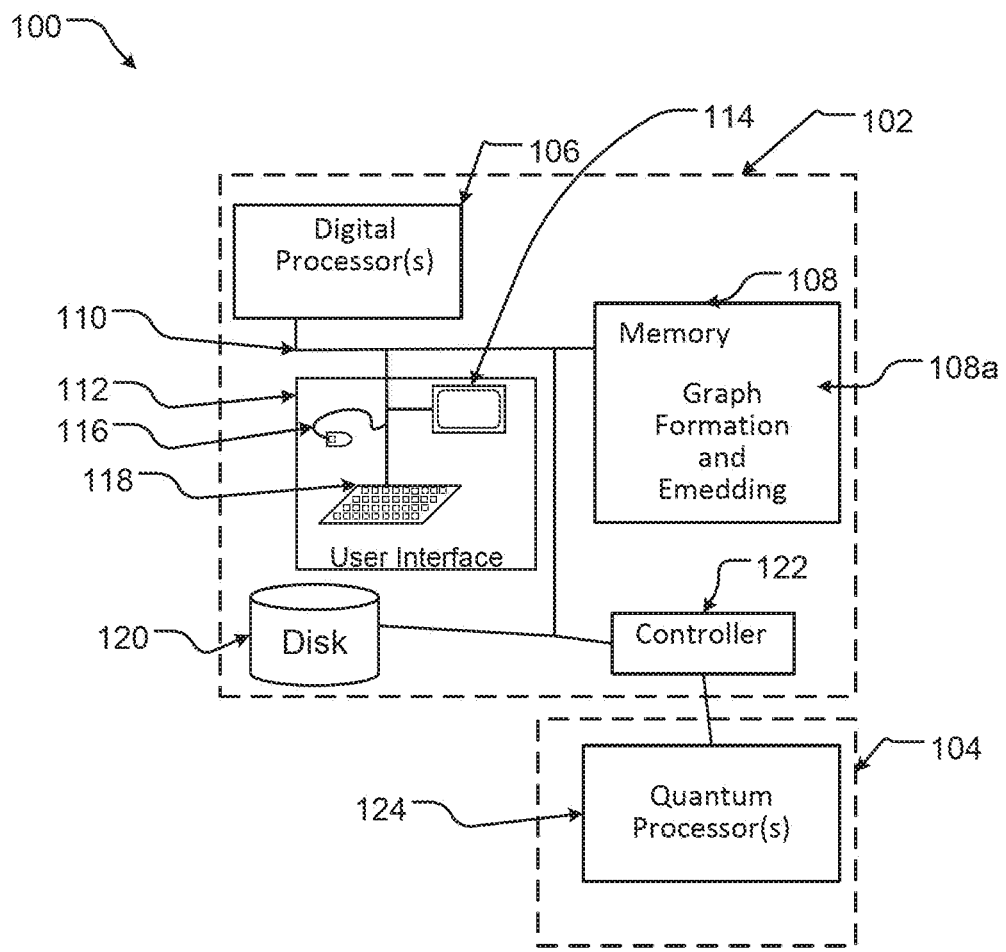
FIG. 1 is a schematic diagram that illustrates an exemplary hybrid computer including a digital processor and an analog processor in accordance with the present systems, devices, methods, and articles.

FIG. 1 illustrates a hybrid computing system 100 including at least one digital computer 102 coupled to at least one analog computer 104. In some implementations the analog computer(s) 104 is a quantum computer.

Determination of natural structures (e.g., nucleic acid sequences) and solution of other problems may advantageously be performed through a combination of classical and analog computing devices, such as, for example, where a classical computing device handles generation of a problem or target graph that represents problem and creation of the Hamiltonian, and a quantum computing device handles the computation of the final state of the Hamiltonian.

Digital computer 102 may include at least one digital processor 106 with one or more cores, that may be used to perform classical digital processing tasks. Digital computer 102 may include at least one nontransitory processor-readable medium, for example system memory 108. Digital computer 102 may include at least one communications channel, for example at least one system bus 110 that couples various system components, including system memory 108 to digital processor 106.

The digital processor 106 may be any circuitry that forms a logic processing unit, such as one or more microprocessors, central processing units ("CPUs"), graphics processing units ("GPUs"), digital signal processors ("DSPs"), application-specific integrated circuits ("ASICs"), programmable gate arrays ("FPGAs"), programmable logic controllers (PLCs), etc.

Digital computer 102 may include a user input/output subsystem 112. In some implementations, the user input/output subsystem 112 includes one or more user input/output components such as a display 114, mouse 116, and/or keyboard 118. While not illustrated, the digital computer 102 will typically include a network interface card (NIC) that provides communications with external devices, for instance with a source of information that represents subsequences or reads of nucleic acids or other information pertaining to other types of problems (e.g., resource allocation problems, traveling salesperson problems).

System bus 110 can employ any known bus structures or architectures, including a memory bus with a memory controller, a peripheral bus, and a local bus.

System memory 108 may include one or more non-volatile memories, such as read-only memory ("ROM"), static random access memory ("SRAM"), Flash NAND; and one or more volatile memories such as random access memory ("RAM") (not shown).

Digital computer 102 may also include other non-transitory computer- or processor-readable storage media 120. Storage media 120 may take a variety of forms, including: spinning media for instance a hard disk drive (HDD) for reading from and writing to a magnetic hard disk and/or an optical disk drive for reading from and writing to removable optical disks, and/or non-spinning media for instance a solid state drive (SSD) for reading from and writing to solid state memory. The optical disk can be a CD-ROM or DVD, while the magnetic disk can be a magnetic floppy disk or diskette or one or more magnetic disc platters. Storage media 120 may communicate with digital processor(s) via system bus 110 and may include appropriate interfaces or controllers 122 coupled to system bus 110. Storage media 120 may serve as long-term storage for processor- or computer-readable instructions, data structures, or other data (sometimes called program modules) for digital computer 102.

Although digital computer 102 has been described as employing hard disks, optical disks and/or magnetic disks, those skilled in the relevant art will appreciate that other types of non-volatile computer-readable media may be employed, such magnetic cassettes, flash memory cards, Flash, ROMs, smart cards, etc. Those skilled in the relevant art will appreciate that some computer architectures employ volatile memory and non-volatile memory. For example, data in volatile memory can be cached to non-volatile memory or in a solid-state drive that employs integrated circuits to provide non-volatile memory.

Various processor- or computer-readable instructions, data structures, or other data can be stored in system memory 108 and/or storage media 120. For example, system memory 108 may store processor-executable graph forming and embedding instructions and/or data 108a that cause the digital processor(s) 106 to convert certain problems into problem graphs, and cause the problem graphs to be embedded in a hardware graph of a quantum processor, for instance as described elsewhere herein. In at least one example provided herein, the processor-executable graph forming and embedding instructions and/or data 108a cause the digital processor(s) 106 to convert a problem of determining or finding a sequence (e.g., sequence of nucleic acid strand) from a plurality of subsequences or sub-strands or reads into a graph representation, and cause the graph representation of the sequencing problem to be embedded in the hardware graph of the quantum processor(s) 104. Also for example, system memory 108 may store processor-executable instructions and/or data that implement communications with remote clients. For example, information or data could be received from or through another computer communicatively coupled to digital computer 102 by a network, for example a local area network (LAN), wide area network (WAN) such as the Internet, other forms of networks, and/or other forms of electronic communication (e.g., Ethernet, parallel cable, or serial connection). Also for example, system memory 108 may store processor-executable instructions and/or data that cause the processor(s) 106 to schedule use of resources, including resources of the digital computer 102 an/or resources of the analog computer 104. In some implementations, system memory 108 may store processor- or computer-readable calculation instructions to perform pre-processing, co-processing, and post-processing. System memory 108 may store at set of analog computer interface instructions to interact with the analog computer 104.

System memory 108 may store an operating system, that includes procedures for handling various system services, such as file services, and for performing hardware-dependent tasks. System memory 108 may store processor-executable instructions and/or data which when executed define a problem to be solved by setting the values of couplings $J_{ij}$ and the local bias $h_i$, adjusting run-time control parameters (such as evolution schedule), scheduling the computation, and acquiring the solution to the problem as an output.

For example, system memory 108 may further include a set of driver instructions that outputs signals to the quantum processor 124. The driver instructions may include a set of mapping instructions, a set of evolution instructions, and a set of output instructions. For example, the mapping instructions may determine the appropriate values of coupling $J_{ij}$ for the coupling devices and values of local bias $h_i$ for the quantum devices of quantum processor 124, for a given problem, as defined by a set of energy function instructions. In some cases, the mapping instructions may include instructions for converting aspects in the energy function Hamiltonian into values for the quantum processor 124, such as coupling strength values and node bias values. The mapping instructions then send the appropriate signals along a bus, into the NIC which, in turn, sends appropriate commands to quantum device control system and a controller.

Alternatively, the evolution instructions may determine the appropriate values of coupling $J_{ij}$ for coupling devices and values of local bias $h_i$ for quantum devices or qubits of the quantum processor 124 in order to fulfill some predetermined evolution. The evolution instructions then sends the appropriate signals along the bus, into the NIC, which then sends commands to a quantum device control system and a coupling device control system. The output instructions are used for processing and providing the solution provided by quantum processor 124.

A NIC may include hardware for interfacing with quantum devices or qubits and coupling devices of quantum processor 124, either directly or through readout devices, to a quantum device control system, and/or a coupling device control system, or software and/or hardware that translates commands from driver instructions into signals (e.g., voltages, currents) that are directly applied to quantum devices or qubits and coupling devices. The NIC may include software and/or hardware that translate signals, representing a solution to a problem or some other form of feedback, from quantum devices or qubits and coupling devices such that it can be provided to the output instructions.

While a number of sets of instructions, modules and data structures resident in system memory 108 have been described, it will be appreciated that at any given time during operation, only a portion of these sets of instructions, modules and/or data structures may, in fact, be resident in system memory 108. In other words, there is no requirement that all or a portion of the sets of instructions, modules and/or data structures be located in system memory 108. In fact, at any given time, all or a portion of the sets of instructions, modules and/or data structures may, in fact, be stored elsewhere, such as in non-volatile storage, or in one or more external computers, not shown in FIG. 1, that are addressable by digital computer 102 across a network (e.g., LAN, WAN such as the Internet or other communications channel).

Furthermore, while the software instructions may be described as a series of modules, it will be appreciated by those of skill in the art that the present systems, methods and apparatus are not limited to the aforementioned combination of software modules. The functions carried out by each of these modules described above may be located in any combination of software or firmware programs, including a single software or firmware program, or a plurality of software or firmware programs and there is no requirement that such programs be structured such that each of the aforementioned modules are present and exist as discrete portions of the one or more software or firmware programs. Such modules have been described simply as a way to best convey how one or more software or firmware programs, operating on computer 102, would interface with processor 106 in order to compute solutions to the various problems.

Analog computer 104 may include at least one analog processor, for example at least one quantum processor 124, for instance a quantum processor that operates at cryogenic temperatures (e.g., at or below −150° C., or even below 1° K) to achieve superconductivity). The analog computer 104 can be provided in an isolated environment, for example, in an isolated environment that shields the internal elements of the quantum computer from heat, magnetic field, and other external noise (not shown) and/or which cools the analog processor to temperatures (i.e., critical temperature, e.g., cryogenic temperatures) at or below which the circuitry of the analog processor becomes superconductive. In contrast, the digital computer 102 will typically operate at much higher temperatures (e.g., room temperature or +20° C.) at which superconductivity does not occur and/or may employ materials that do not superconduct even at or below the critical temperature.

The analog computer 104 may include a readout device. In some embodiments, the readout device may include a plurality of dc-SQUID magnetometers, each inductively connected to a different quantum device. In such cases, a NIC may receive a voltage or current from readout device, as measured by each dc-SQUID magnetometer in readout device. The analog computer 104 may also include a controller that includes a coupling control system for each coupling device, each coupling control system in the control device being capable of tuning the coupling strength of its corresponding coupling device through a range of values, such as between $-|J_c|$ to $+|J_c|$, where $|J_c|$ is a maximum coupling value. The analog computer 104 may include a quantum device control system that includes a control device capable of tuning characteristics (e.g., values of local bias $h_i$) of a corresponding quantum device.

Figure 2:
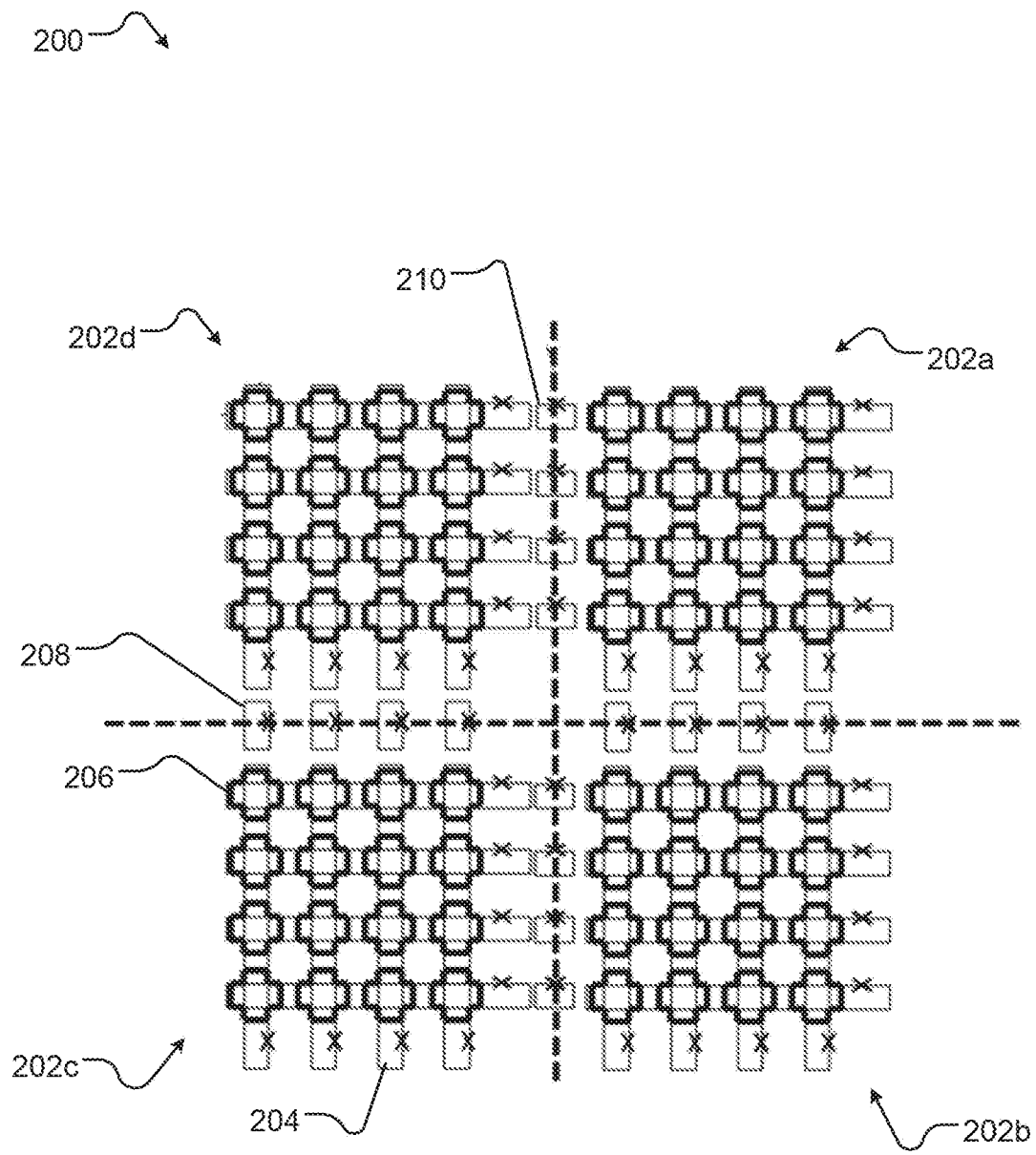
FIG. 2 is a schematic diagram that illustrates a portion of an exemplary topology, suitable for implementing the analog computer of FIG. 1, for example via quantum annealing in accordance with the present systems, devices, articles, and methods.

FIG. 2 shows an exemplary topology 200 for a quantum processor, in accordance with the presently described systems, devices, articles, and methods. Topology 200 may be used to implement quantum processor 124 of FIG. 1, however other topologies can also be used for the systems and methods of the present disclosure. Topology 200 comprises a grid of 2×2 cells such as cells 202a, 202b, 202c and 202d (collectively 202), each cell comprised of eight qubits such as qubit 204 (only one called out in FIG. 2).

Within each cell 202, there are eight qubits 204, the qubits 204 in each cell 202 arranged in four rows (extending horizontally in drawing sheet) and four columns (extending vertically in drawing sheet). Pairs of qubits 204 from the rows and columns can be communicatively coupled to one another by a respective coupler such as coupler 206 (illustrated by bold cross shapes, only one called out in FIG. 2). A respective coupler 206 is positioned and operable to communicatively couple the qubit in each column (vertically-oriented qubit in drawing sheet) in each cell to the qubits in each row (horizontally-oriented qubit in drawing sheet) in the same cell. Additionally, a respective coupler, such as coupler 208 (only one called out in FIG. 2), is positioned and operable to communicatively couple the qubit in each column (vertically-oriented qubit in drawing sheet) in each cell with a corresponding qubit in each column (vertically-oriented qubit in drawing sheet) in a nearest neighboring cell in a same direction as the orientation of the columns. Similarly, a respective coupler, such as coupler 210 (only one called out in FIG. 2), is positioned and operable to communicatively couple the qubit in each row (horizontally-oriented qubit in drawing sheet) in each cell with a corresponding qubit in each row (horizontally-oriented qubit in drawing sheet) in each nearest neighboring cell in a same direction as the orientation of the rows. While couplers 206 are illustrated by bold cross shapes, such is not intended to be limiting, and couplers 206 can have any of a variety of other shapes.

While a quantum device can, for example, take the form of a superconducting qubit or coupler, a suitable quantum device may be any other technology or structure that supports quantum information processing and quantum computing, such as electrons on liquid helium, nuclear magnetic resonance qubits, quantum dots, donor atoms (spin or charges) in semiconducting substrates, linear and non-linear optical systems, cavity quantum electrodynamics, and ion and neutral atom traps.

Where the quantum device is a superconducting qubit, the physical characteristics of quantum device include capacitance (C), inductance (L), and critical current ($I_C$), which are often converted into two values, the Josephson energy ($E_J$) and charging energy ($E_C$), and a dimensionless inductance ($\beta_L$). Those of skill in the art will appreciate that the relative values of these quantities will vary depending on the configuration of quantum device. For example, where the quantum device is a superconducting flux qubit or a flux qubit, the thermal energy ($k_BT$) of the qubit may be less than the Josephson energy of the qubit, the Josephson energy of the qubit may be greater than the charging energy of the qubit, or the Josephson energy of the qubit may be greater than the superconducting material energy gap of the materials of which the qubit is composed. Alternatively, where the quantum device is a superconducting charge qubit or a charge qubit, the thermal energy of the qubit may be less than the charging energy of the qubit, the charging energy of the qubit may be greater than the Josephson energy of the qubit, or the charging energy of the qubit may be greater than the superconducting material energy gap of the materials of which the qubit is composed. In still another alternative, where the quantum device is a hybrid qubit, the charging energy of the qubit may be about equal to the Josephson energy of the qubit. See, for example, U.S. Pat. No. 6,838,694 and U.S. Patent Publication No. 2005-0082519, each of which is hereby incorporated by reference in its entirety.

Quantum devices may include a superconducting loop interrupted by one or more Josephson junctions, e.g., three Josephson junctions. Current can flow around a loop in either a clockwise direction or a counterclockwise direction, and in some embodiments, the direction of current may represent the state of a quantum device. Unlike classical devices, current can flow in both directions of a superconducting loop at the same time, thus enabling the superposition property of qubits. Bias devices are located in proximity to the quantum device and inductively bias the magnetic flux through the loop of quantum device. By changing the flux through the loop, the characteristics of the quantum device can be tuned.

Quantum devices may have fewer or more than three Josephson junctions. For example, quantum devices may have only a single Josephson junction, a device that is commonly known as an rf-SQUID (i.e., "superconducting quantum interference device"). Alternatively, quantum devices may have two Josephson junctions, a device commonly known as a dc-SQUID. See, for example, Kleiner et al., 2004, *Proc. of the IEEE* 92, pp. 1534-1548; and Gallop et al., 1976, *Journal of Physics E: Scientific Instruments* 9, pp. 417-429.

The potential energy landscape of a quantum device may, for example, include two potential wells separated by a tunneling barrier. The wells correspond to the directions of current flowing in the quantum device. One current direction corresponds to one well, while the other current direction corresponds to the other well. By tuning the magnetic flux through the loop, the relative depth of the potential wells can be changed. Thus, with appropriate tuning, one well can be made much shallower than the other. This may be advantageous for initialization and measurement of the qubit.

Many of the processes for fabricating superconducting circuits are the same as, or similar to, those established for semiconductor-based circuits. Niobium (Nb) and aluminum (Al) are superconducting materials common to superconducting circuits; however, there are many other superconducting materials any of which can be used to construct the superconducting aspects of quantum device. Josephson junctions that include insulating gaps interrupting the loop can be formed using insulating materials such as aluminum oxide or silicon oxide to form the gaps.

Figure 3A:
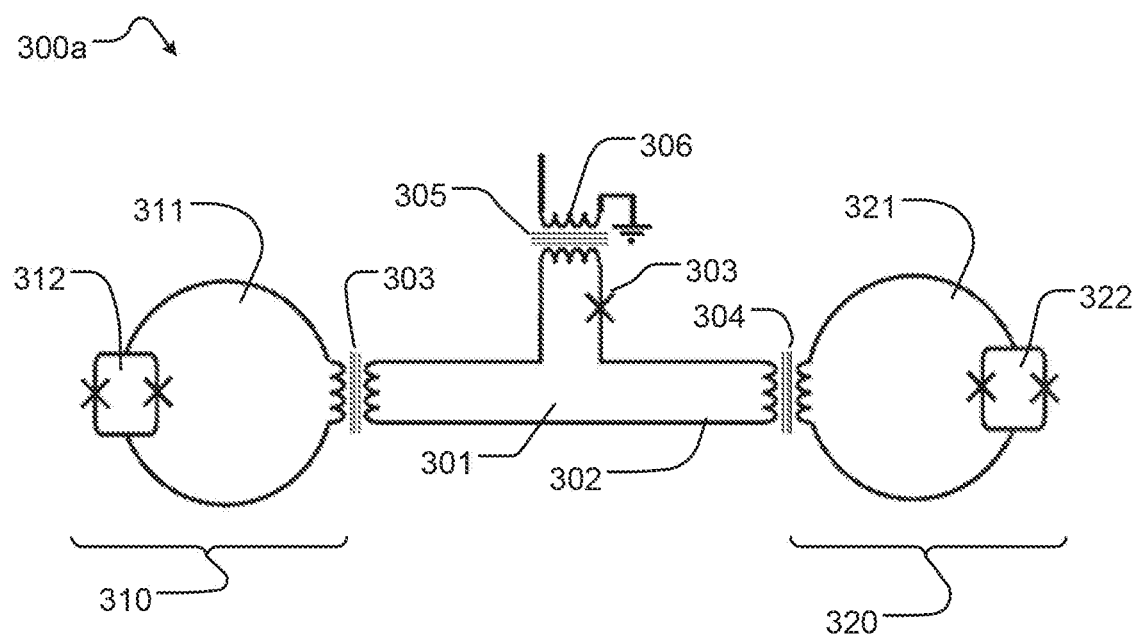
FIG. 3A shows a schematic diagram of a controllable ZZ-coupler, suitable for implementing the topology of FIG. 2.

FIG. 3A shows an exemplary implementation of a system 300a comprising a controllable ZZ-coupler 301. Controllable ZZ-coupler 301 includes a loop of superconducting material 302 interrupted by a Josephson junction 303 and is used to couple a first qubit 310 and a second qubit 320. First qubit 310 is comprised of a loop of superconducting material (or "qubit loop") 311 interrupted by a compound Josephson junction ("CJJ") 312 and is coupled to controllable ZZ-coupler 301 through the exchange of flux 303 between controllable ZZ-coupler 301 and first qubit 310. Second qubit 320 is comprised of a loop of superconducting material (or "qubit loop") 321 interrupted by a CJJ 322 and is coupled to controllable ZZ-coupler 301 through the exchange of flux 304 between controllable ZZ-coupler 301 and second qubit 320. Loop of superconducting material 302 is threaded by flux 305 created by electrical current flowing through a magnetic flux inductor 306. Controllable ZZ-coupler 301 may be used in in topology 200 to provide communicative coupling between qubits and, thus, be used in a quantum processor, in accordance with the presently described systems, devices, articles, and methods.

Variations and, for some applications, improvements to the ZZ-coupler design shown in FIG. 3A are presented in U.S. Pat. Nos. 7,898,282 and 7,800,395.

Figure 3B:
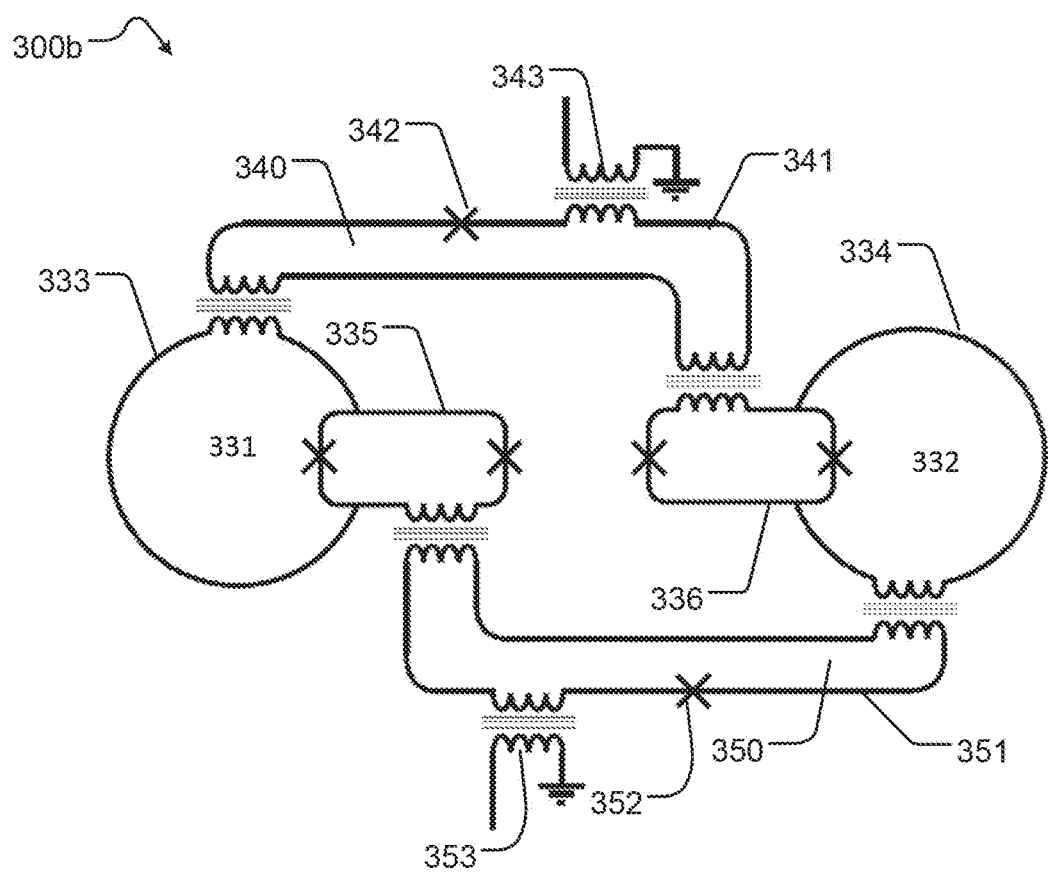
FIG. 3B is a schematic diagram of an embodiment of a system that includes two superconducting qubits and both a ZX-coupler and an XZ-coupler, each of which is operable to communicably couple information between the two qubits, suitable for implementing the topology of FIG. 2.

FIG. 3B shows an exemplary implementation of a system 300b that includes two superconducting qubits 331, 332 and both a ZX-coupler 340 and an XZ-coupler 350, each of which is configured to communicably couple information between qubits 331 and 332. Each qubit 331, 332 includes a qubit loop 333, 334, respectively, formed by a closed superconducting current path that is interrupted by a CJJ 335, 336, respectively.

ZX-coupler 340 includes a closed superconducting current path 341 that is inductively coupled to both the qubit loop 333 of qubit 331 and the CJJ 336 of qubit 332. Thus, ZX-coupler 340 provides coupling between the Z-degree of freedom in qubit 331 and the X-degree of freedom in qubit 332 by inductively coupling the persistent current in the qubit loop 333 of qubit 331 into the CJJ 336 of qubit 332.

In the case of ZX-coupler 340, tunability is realized by two tuning elements: closed superconducting current path 341 is interrupted by at least one Josephson junction 342 and closed superconducting current path 341 is inductively coupled to a programming interface 343.

Similarly, XZ-coupler 350 includes a closed superconducting current path 351 that is inductively coupled to both the qubit loop 334 of qubit 332 and the CJJ 335 of qubit 331. Thus, XZ-coupler 350 provides coupling between the X-degree of freedom in qubit 331 and the Z-degree of freedom in qubit 332 by inductively coupling the persistent current in the qubit loop 334 of qubit 332 into the CJJ 335 of qubit 331.

Both XZ-coupler 350 and ZX-coupler 340 may also be made tunable by the combination of two tuning elements: closed superconducting current path 351 is interrupted by at least one Josephson junction 352 and inductively coupled to a programming interface 353, while closed superconducting current path 341 is interrupted by at least one Josephson Junction 342 and inductively coupled to a programming interface 343.

System 300b may be used in topology 200 to provide communicative coupling between qubits and, thus, be used in a quantum processor, in accordance with the presently described systems, devices, articles, and methods.

Example 1

Figure 4A:
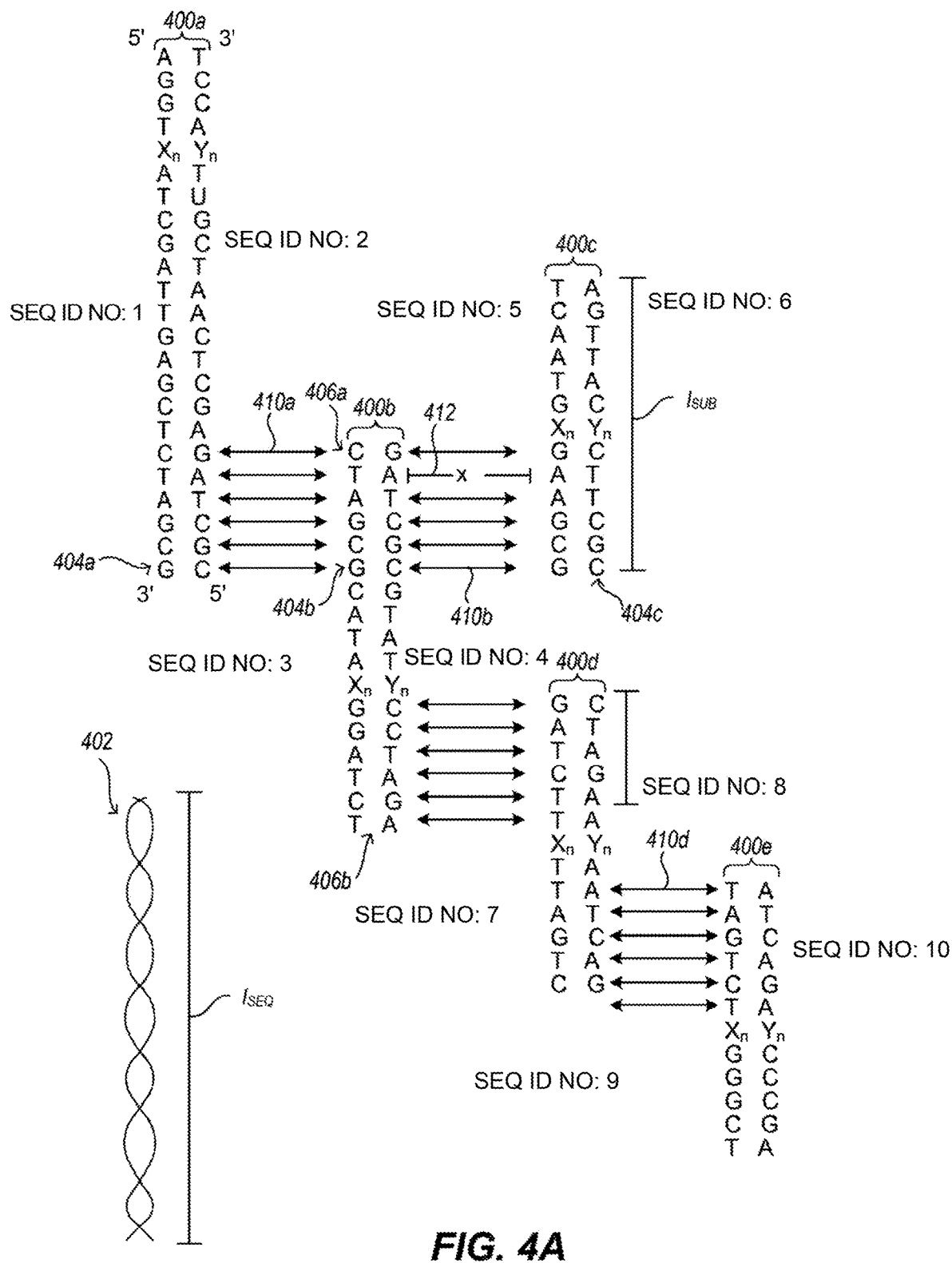
FIG. 4A is a schematic diagram of a number of subsequences or "reads" of a DNA sequence (SEQ ID NOS:1-10), illustrating for each of a plurality of pairs of reads a match between base pairs of a portion (i.e., overlapping portion) of the reads of the respective pair of reads, and for at least one pair of reads a lack of match between the base pairs of a portion of the reads of the pair of reads, the matches identified in accordance with the present systems, devices, articles, and methods.

FIG. 4A shows a number of reads or subsequences 400a [SEQ ID NOS: 1 and 2], 400b [SEQ ID NOS: 3 and 4], 400c [SEQ ID NOS: 5 and 6], 400d [SEQ ID NOS: 7 and 8], 400e [SEQ ID NOS: 9 and 10] (only five shown, collectively 400) of an exemplary DNA sequence 402, with a number of matches between portions of some pairs of reads and a lack of match between a pair of reads 400b, 400c, the matches identified in accordance with the present systems, devices, articles, and methods. The subsequences 400a-400e are made up for illustrative purposes and do not necessarily represent any naturally occurring sequence, and thus may be artificial sequences.

A DNA strand or sequence 402 is typically represented as a sequence of base pairs 404a, 404b, 404c (e.g., GC, only three called out to avoid clutter in the drawing, collectively 404). The base pairs 404 are units of two nucleobases, bound to each other via hydrogen bonds. Watson-Crick base pairs for DNA are: i) guanine-cytosine, and ii) adenine-thymine. The nucleobases are represented by of four letters G, C, A, T, each letter representing a respective nucleobase guanine, cytosine, adenine, and thymine, respectively. The four possible base pairs for DNA typically include the combinations of nucleobases: GC, CG, AT, TA.

An entire DNA strand or sequence 402 may be processed as part of performing sequencing, at least part of the processing resulting in breaking up the DNA strand or sequence 402 into subsequences or snippets of DNA. In practice, a large number of DNA strands or sequences 402 are broken up and processed, the DNA strands or sequences 402 being from a single subject and, thus, typically being identical to one another. In many instances, a DNA strand or sequence 402 may be quite long, for instance having a length $l_{SEQ}$ of millions or even billions of base pairs 404. Thus, a very large number $N_{READS}$ of subsequences or snippets 400 can result. The resulting subsequences or snippets 400 can have a large variety of individual respective lengths (i.e., number of base pairs included in the subsequence or snippet) $l_{SUB}$. As part of the sequencing process, the base pairs 404 of the resulting subsequences or snippets 400 are identified using any of a variety of techniques including, for example, two-dimensional chromatography or fluorescence-based sequencing using a DNA sequencer. The result is subsequences 400 of base pairs 404, commonly referred to as reads 400, again typically in the form of sequences of the base pairs GC, CG, AT, TA, which may for instance be represented in a digital or electronic file. There may be many reads 400, and the reads may have a variety of different lengths (i.e., number of base pairs included in the subsequence). It is noted that the term read or reads 400 is commonly used interchangeably with the terms subsequence or subsequences 400 or even with the terms snippet or snippets.

For ease of illustration, FIG. 4A shows only a portion of the subsequences or reads 400 resulting from processing of a DNA strand or sequence 402. In particular, FIG. 4A only shows five subsequences or reads resulting from the processing, namely a first read 400a, second read 400b, third read 400c, fourth read 400d and fifth read 400e. The reads 400 are represented with a number of base pairs 404 at a first end 406a (only one called out) and a number of base pairs at a second end 406b (only one called out), the second end 406b opposed to the first end 406a across a respective length $l_{SUB}$ (only one called out) of the read 400. Each read 400 is illustrated with a respective set of values $X_N$, $Y_N$ to indicate that there may be none, one, or any number of additional pairs of nucleobases between the base pairs 404 illustrated at the first and the second ends 406a, 406b of the respective read 400, where X is a nucleobase selected from guanine, cytosine, adenine, and thymine, Y is a nucleobase selected from guanine, cytosine, adenine, and thymine, and N is a value from 0 to $1 \times 10^{10}$. As previously noted, reads 400 can have a large variety of lengths.

In order to determine the sequence of the original DNA strand or sequence 402, the various subsequences or reads 400 are processed to piece the subsequences or reads 400 together in the correct order or sequence. Such can be performed by looking for overlapping segments or portions of the subsequences or reads 400 with a defined number $N_{OVERLAP}$ of base pairs 404 that match. In particular, matches for a defined number $N_{OVERLAP}$ of base pairs 404 at one end 406b of a first subsequence or read 400 is sought at an end 406a of one of the other subsequences or reads 400. For instance, the other subsequences or reads may be evaluated to find any with, for example, six base pairs 404 at a first end 406a, which match the six base pairs 404 at a second end 406b of the first subsequence or read 400. Finding subsequences or reads 400 with sufficient overlap in base pairs 404 allows the original DNA strand or sequence 402 to be pieced together from the subsequences or reads 400. Such can advantageously be accomplished using the algorithms, techniques and hardware described herein. While the number $N_{OVERLAP}$ of desired overlap in base pairs has been illustrated as being equal to at least five, almost any other integer could be selected given the specific application and problem to which the algorithm and techniques will be applied.

In FIG. 4A, matches between base pairs 404 are illustrated by double headed arrows 410a, 410b, 410c, 410d (only four called out for clarity of illustration, collectively 410). A lack of a match between base pairs 404 is illustrated by a line with a cross or X therein 412 (only one illustrated). Thus, where the defined number or length $N_{OVERLAP}$ of overlap is set to $N_{OVERLAP}=5$, the second subsequence or read 400b follows the first subsequence or read 400a, the fourth subsequence or read 400d follows the second subsequence or read 400b, and the fifth subsequence or read 400e follows the fourth subsequence or read 400d. The third subsequence or read 400b is not in the ordered sequence between the first and the fifth subsequences or reads 400a, 400e and, thus, is presumably located elsewhere in the original DNA strand or sequence 402. Again, only five of what may be a very large number of subsequences or reads 400 are illustrated to prevent clutter of the drawing. An algorithm to perform the matching is described in FIG. 5, and executable via the hardware described herein, for instance the hardware described with respect to FIGS. 1, 2, 3A and 3B.

Figure 4B:
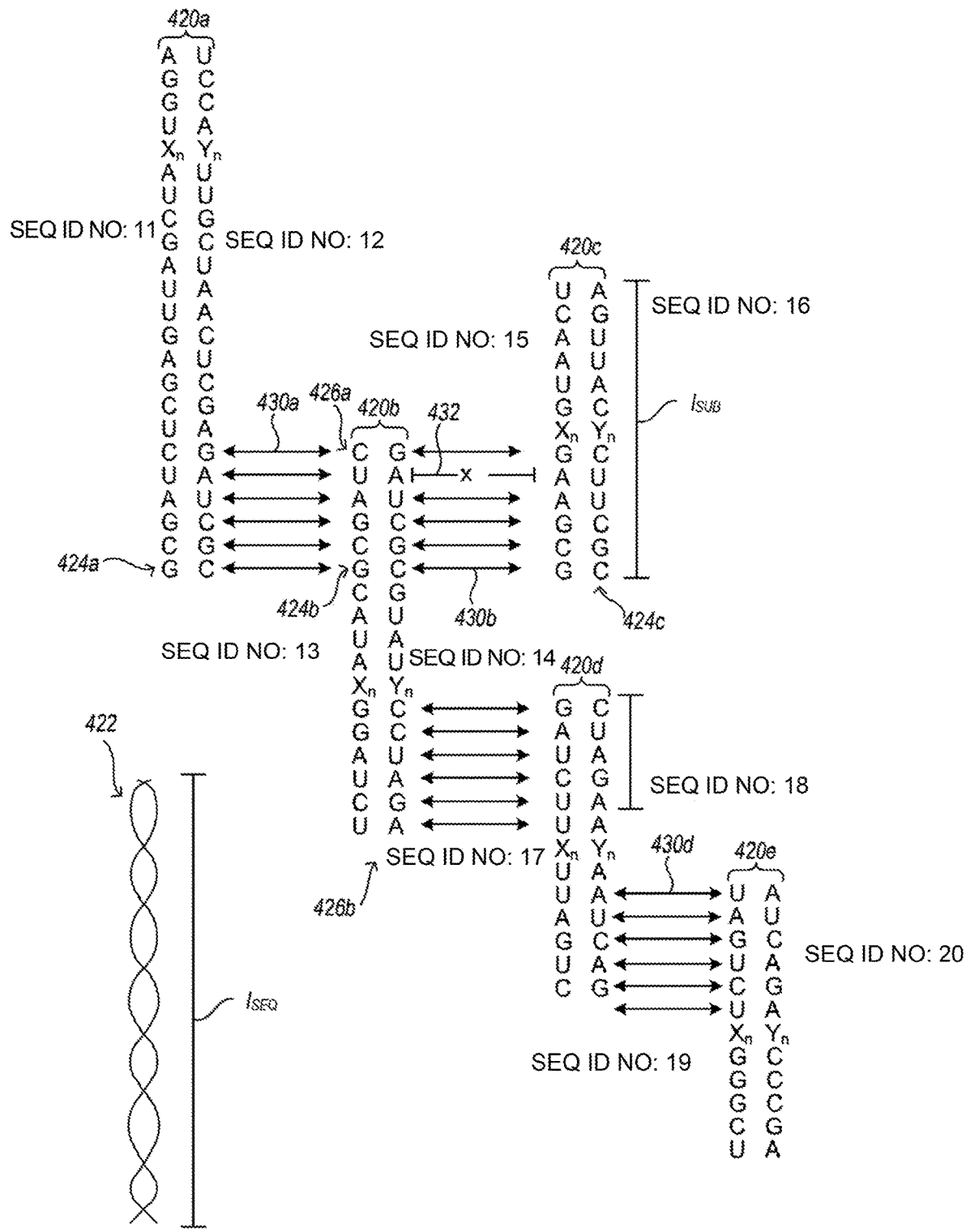
FIG. 4B is a schematic diagram of a number of subsequences or "reads" of a RNA sequence (SEQ ID NOS:11-20), illustrating for each of a plurality of pairs of reads a match between base pairs of a portion (i.e., overlapping portion) of the reads of the respective pair of reads, and for at least one pair of reads a lack of match between the base pairs of a portion of the reads of the pair of reads, the matches identified in accordance with the present systems, devices, articles, and methods.

FIG. 4B shows a number of reads or subsequences 420a [SEQ ID NOS: 11 and 12], 420b [SEQ ID NO: 13 and 14], 420c [SEQ ID NOS: 15 and 16], 420d [SEQ ID NOS: 17 and 18], 420e [SEQ ID NOS: 19 and 20] (only five shown, collectively 420) of an exemplary RNA sequence 422, with a number of matches between some portions of pairs of reads 420 and a lack of match between a pair of reads 420b, 420c, the matches identified in accordance with the present systems, devices, articles, and methods. The subsequences 420a-420e are made up for illustrative purposes and do not necessarily represent any naturally occurring sequence.

An RNA strand or sequence 402 is typically represented as a sequence of base pairs 424a, 424b, 424c (e.g., GC, only three called out to avoid clutter in the drawing, collectively 424). The base pairs 424 are units of two nucleobases, bound to each other via hydrogen bonds. Watson-Crick base pairs for RNA are: i) guanine-cytosine, and ii) adenine-uracil. The nucleobases are represented by of four letters G, C, A, U, each letter representing a respective nucleobase guanine, cytosine, adenine, and uracil, respectively. The four possible base pairs for RNA typically include the combinations of nucleobases: GC, CG, AU, UA.

An entire RNA strand or sequence 422 may be processed as part of performing sequencing, at least part of the processing resulting in breaking up the RNA strand or sequence 422 into subsequences or snippets of RNA. In practice, a large number of RNA strands or sequences 422 are broken up and processed, the RNA strands or sequences 422 being from a single subject and, thus, typically being identical to one another. In many instances, an RNA strand or sequence 422 may be quite long, for instance having a length $l_{SEQ}$ of millions or even billions of base pairs 424. Thus, a very large number M of subsequences or snippets 420 can result. The resulting subsequences or snippets 420 can have a large variety of individual respective lengths (i.e., number of base pairs included in the subsequence or snippet) $l_{SUB}$. As part of the sequencing process, the base pairs 424 of the resulting subsequences or snippets 420 are identified using any of a variety of techniques including, for example, two-dimensional chromatography or fluorescence-based sequencing using an RNA sequencer. The result is subsequences 420 of base pairs 424, commonly referred to as reads 400, again typically in the form of sequences of the base pairs GC, CG, AU, TU, which may, for instance, be represented in a digital or electronic file. There may be many reads, and the reads may have a variety of different lengths (i.e., number of base pairs included in the subsequence). It is noted that the term read or reads 400 is commonly used interchangeably with the terms subsequence or subsequences 400 or even with the terms snippet or snippets.

For ease of illustration, FIG. 4B shows only a portion of the subsequences or reads 420 resulting from processing of an RNA strand or sequence 422. In particular, FIG. 4B only shows five subsequences or reads resulting from the processing, namely a first read 420a, second read 420b, third read 420c, fourth read 420d and fifth read 420e. The reads 420 are represented with a number of base pairs 424 at a first end 426a and a number of base pairs 424 at a second end 426b, the second end 426b opposed to the first end 426a across a respective length $l_{SUB}$ of the read 420. Each read 420 is illustrated with a respective set of values $X_N$, $Y_N$ to indicate that there may be none, one, or any number of additional pairs of nucleobases between the base pairs 404 illustrated at the first and the second ends 406a, 406b of the respective read 400, where X is a nucleobase selected from guanine, cytosine, adenine, and uracil, Y is a nucleobase selected from guanine, cytosine, adenine, and uracil, and N is a value from 0 to $1 \times 10^{10}$. As previously noted, reads 420 can have a large variety of lengths.

In order to determine the sequence of the original RNA strand or sequence 422, the various subsequences or reads 420 are processed to piece the subsequences or reads 420 together in the correct order or sequence. Such can be performed by looking for overlapping segments or portions of the subsequences or reads 420 with a defined number $N_{OVERLAP}$ of base pairs 424 that match. In particular, matches for a defined number $N_{OVERLAP}$ of base pairs 424 at one end 426b of a first subsequence or read 420 is sought at an end 426a of one of the other subsequences or reads 420. For instance, the other subsequences or reads 420 may be evaluated to find any with, for example, six base pairs 424 at a first end 426a, which match the six base pairs 424 at a second end 426b of the first subsequence or read 420. Finding subsequences or reads 420 with sufficient overlap in base pairs 424 allows the original DNA strand or sequence 422 to be pieced together from the subsequences or reads 420. While the number $N_{OVERLAP}$ of desired overlap in base pairs has been illustrated as being equal to at least five, almost any other integer could be selected given the specific application and problem to which the algorithm and techniques will be applied.

In FIG. 4B, matches between base pairs 424 are illustrated by double headed arrows 430a, 430b, 430c, 430d (only four called out for clarity of illustration, collectively 430). A lack of a match between base pairs 424 is illustrated by a line with a cross or X therein 432 (only one illustrated). Thus, where the defined number or length $N_{OVERLAP}$ of overlap is set to $N_{OVERLAP}=5$, the second subsequence or read 420b follows the first subsequence or read 420a, the fourth subsequence or read 420d follows the second subsequence or read 420b, and the fifth subsequence or read 420e follows the fourth subsequence or read 420d. The third subsequence or read 420b is not in the ordered sequence between the first and the fifth subsequences or reads 420a, 420e and, thus, is presumably located elsewhere in the original DNA strand or sequence 422. Again, only five of what may be a very large number of subsequences or reads are illustrated to prevent clutter. An algorithm to perform the matching is described in FIG. 5, and executable via the hardware described herein, for instance the hardware described with respect to FIGS. 1, 2, 3A and 3B.

Figure 5:
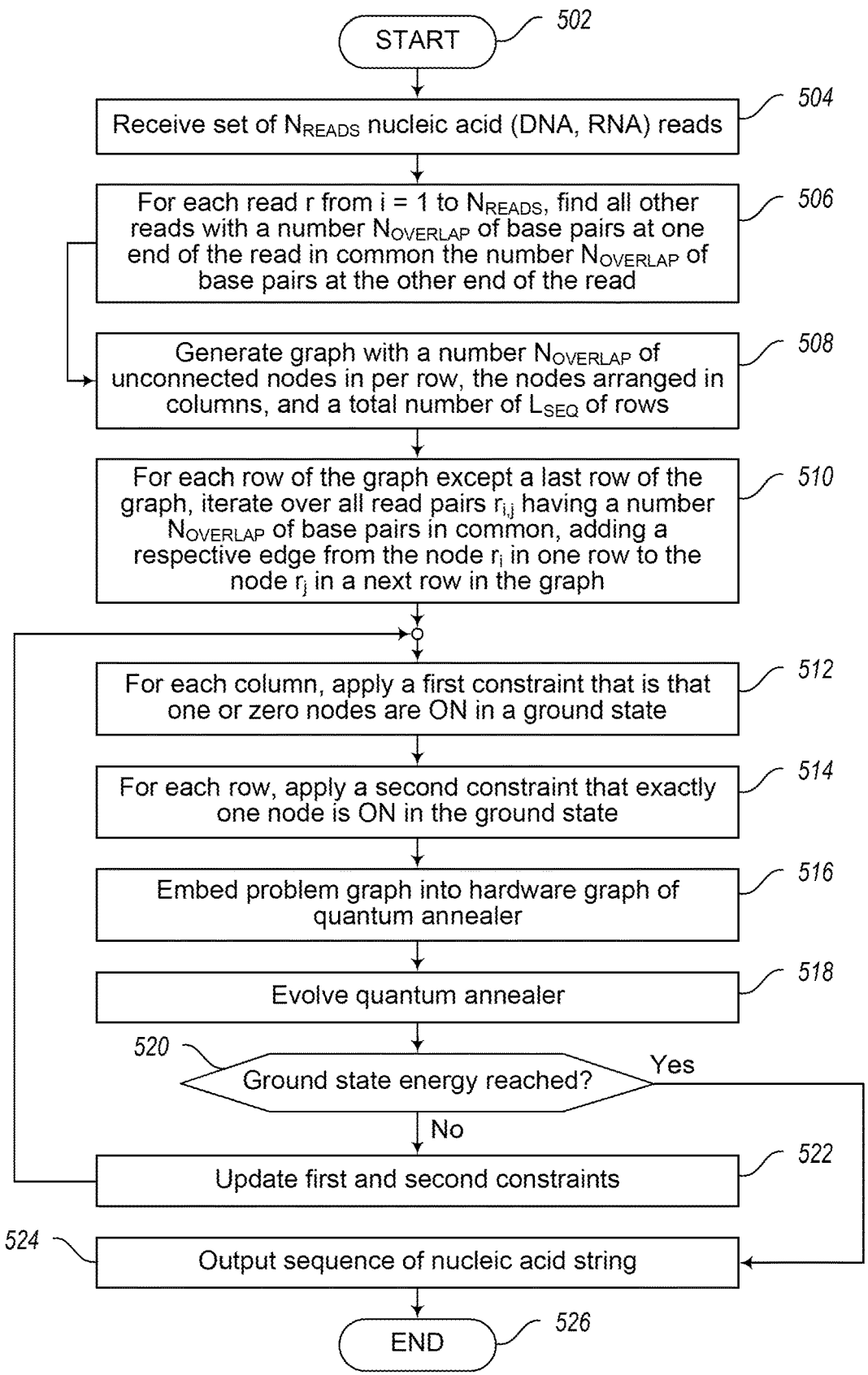
FIG. 5 is a flow diagram that shows a method for performing machine learning by sampling from a sampling server in accordance with the present systems, devices, articles, and methods.

FIG. 5 shows a method 500 of converting certain problems into problem graphs, and causing the problem graphs to be embedded in a hardware graph of a quantum processor to search for solutions to the problem, in accordance with the present systems, devices, articles, and methods.

The method 500 starts at 502, for example in response to receiving a problem, for instance a nucleic acid sequencing problem or other problem. The problem can be received from another system, for example from a sequencer that generates reads in electronic form.

At 504, at least one component of a system receive a set of nucleic acid (DNA, RNA) reads. For example, a digital computer of the system can receive the set of reads. The set may include a total number $N_{READS}$ of nucleic acid subsequences or reads. Alternatively, the set can include a total number of other types of subsequences of a total sequence.

At 506, for each of the reads $r_i$ from I=1 to the total number of reads $N_{READS}$, at least one component of the system finds all other reads $r_j$ with a defined number $N_{OVERLAP}$ of base pairs present at one end of the read $r_j$ which are in common with (i.e., respectively match) the number $N_{OVERLAP}$ of base pairs at the other end of the read $r_i$. For example, a digital computer of the system can find the reads with ends that "overlap" a given read by a defined amount. The term overlap as used herein means that two or more subsequences have an identical pattern over a defined portion or length thereof, preferably proximate an end of the subsequence. For instance, a second subsequence may have the same five base pairs at one end as the five base pairs at another end of a first subsequence.

At 508, at least one component of the system generates a problem or target graph with a number $N_{OVERLAP}$ of unconnected nodes per row, where the nodes are arranged in columns, and the graph has a total number of $L_{SEQ}$ of rows. For example, a digital computer of the system can generate the problem or target graph.

At 510, for each row of the graph except a last row of the graph, at least one component of the system iterates over all read pairs $r_{i,j}$ having a number $N_{OVERLAP}$ of base pairs in common, adding a respective edge from the node $r_i$ in one row to the node $r_j$ in a next row in the graph. For example, a digital computer of the system can perform the iteration.

At 512, for each column, at least one component of the system applies a first constraint. The first constraint being that one or zero nodes are ON in a ground state. For example, a digital computer of the system can apply the first constraint.

At 514, for each row, at least one component of the system applies a second constraint. The second constraint being that exactly one node is ON in the ground state. For example, a digital computer of the system can apply the second constraint. Thus, an energy function may be created, which will be minimized to determine the lowest energy configuration of the matching of the subsequences, as a predictor of the native structure or sequential order. This energy function is created based on the constraints and interactions to be included as part of the model. Those of skill in the art will appreciate that many other constraints and interactions may be included as part of the energy function.

At 516, at least one component of the system embeds the resultant problem or target graph into a hardware graph of a quantum annealer. For example, a digital computer of the system can embed the problem or target graph into the hardware graph if a quantum processor via one or more interfaces. Various techniques for embedding a problem or target graph are described in patent applications and patents assigned to D-WAVE SYSTEMS and incorporated herein by reference in their entirety, as well as non-patent literature published by D-WAVE SYSTEMS and/or authored by its employees.

At 518, at least one component of the system evolves a quantum annealer, for example, adiabatically evolving the quantum processor toward a ground state. In order to solve the problem, a natural physical evolution of the analog processor is performed to transition the analog processor from an initial state to a final state which represents the energy function corresponding to an ordered sequence of the subsequences or reads. The final state may be a ground state representing a minimization of the energy function. Following evolution, reading out the state of the analog processor will return a set of bit strings which represent the ordered sequence of base pairs in the primary structure (e.g., strand, sequence or string of a nucleic acid) in the minimum energy configuration, representing the predicted native structure of the primary structure.

At 520, at least one component of the system determines whether a ground state energy has been reached.

If it is determined that a ground state energy has not been reached, then at least one component of the system updates the first and the second constraints at 522, and control passes back to 512.

If it is determined that a ground state energy has been reached, then at least one component of the system outputs a sequence at 524. The sequence is generated from the reads or subsequences. The sequence, for example, represents part or all of a nucleic acid strand or sequence.

The method 500 terminates at 526, for example until called or invoked again. In some implementations, the method 500 repeats multiple times until a consensus of a plurality of solutions is realized.

Figure 6A:
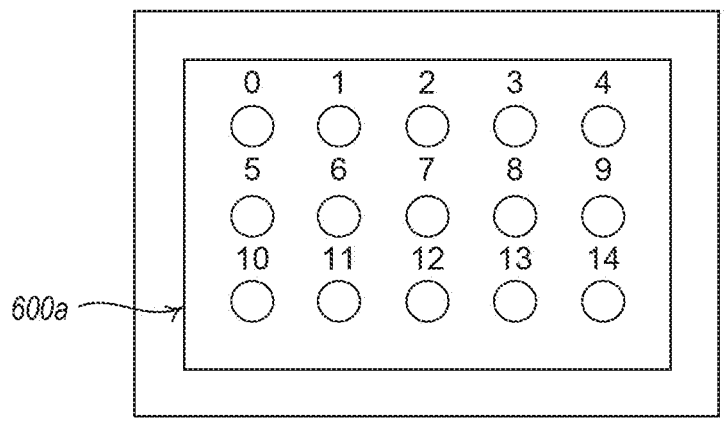
FIGS. 6A-6C are schematic diagrams sequentially illustrating creation of a problem or target graph of a QUBO representation of a problem such as a nucleic acid sequencing problem, in accordance with the present systems, devices, articles, and methods.
Figure 6B:
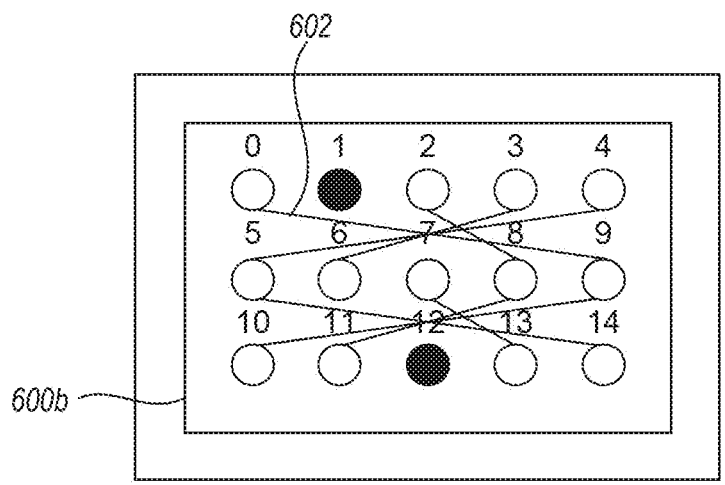
Figure 6C:
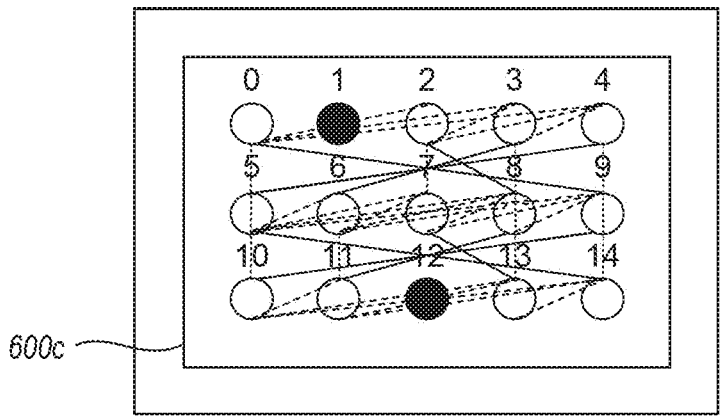

FIGS. 6A-6B are schematic diagrams sequentially illustrating creation of a problem or target graph 600c of a QUBO representation of a problem such as a nucleic acid sequencing problem, in accordance with the present systems, devices, articles, and methods. In particular, FIGS. 6A-6C illustrate a simplified example where the number of reads $N_{READS}$ is equal to five (5) and the length of an entire sequence $l_{SEQ}$ is equal to three (3). The concepts and techniques represented herein can, of course, be easily expanded to larger and much more complicated examples or applications. The use of a quantum annealer may advantageously allow the approach and techniques to readily scale with larger and much more complicated examples or applications, including nucleic acid sequencing for nucleic acid strands or sequences of millions or even billions of base pairs.

In particular, FIG. 6A shows initial formation of a graph 600a, which includes a plurality of nodes 1-14, which may be arranged in rows and columns. The nodes, for example, can be arranged with a total of nodes in each row (i.e., equal to the total number of columns) equal to the number of reads $N_{READS}$, and with the total number of nodes in each column (i.e., equal to the total number of rows) equal to length of the sequence $l_{SEQ}$. Such can for instance result from performance of acts 504, 506 and/or 508 of the method 500 (FIG. 5).

In particular, FIG. 6B shows an addition of overlap edges 602 (illustrated in FIG. 6B by lines extending between pairs of nodes, only one called out in FIG. 6B to prevent clutter) between selected nodes of the graph 600a to produce the graph 600b. For example, such can include adding edges between pairs of nodes where the two nodes of the pair represent respective subsequences or reads with overlap (i.e., matches between a defined number $N_{OVERLAP}$ of corresponding values, e.g., between ten (10) base pairs). Such can, for instance, result from performance of act 510 of the method 500 (FIG. 5). In this example, there are two nodes 1, 12 without edges extending thereto or therefrom.

In particular, FIG. 6C shows the addition of constraints to the graph 600b to realize the problem or target graph 600c. In this example, first and second constraints are added. Such can for instance result from performance of acts 512, 514 of the method 500 (FIG. 5).

The ground state energy for this example problem is given as 1−2|=−5. There is exactly one ground state {2, 8, 22}. This means there is exactly one valid combination (i.e., sequence of reads with specified overlap at ends or reads) of three (3) reads using the original five (5) reads.

A set of instructions suitable to implement various techniques and algorithms described herein follows immediately below.

```
import numpy as np
import itertools
class Read(object):
    def __init__(self, bases):
        # Bases in the read
        self.bases = bases
    def __repr__(self):
        return self.bases
    def overlaps(self, read, num_bases=10):
        """
        Determines if the read overlaps with a given read.
                        Directionality is always from this
                        read to parameter read.
        :param read: read to compare to
        :param num_bases: number of bases of overlap required
        :return: Boolean
        """
        return self.bases[-num_bases:] == 
                        read.bases[:num_bases]
class SequenceAssembly(object):
    def __init__(self, reads, overlap, path_length):
        """
        Construct a sequence assembly object.
        :param reads: list of strings. each string is a read.
        :param overlap: number of bases that must overlap.
        :param path_length: length of path to be considered
                        in this decision problem.
        :return:
        """
        self.path_length = path_length
        self.num_reads = len(reads)
        self.reads = list( )
        for bases in reads:
            self.reads.append(Read(bases))
        self.edges = set( )
        for i, read1 in enumerate(self.reads):
            for j, read2 in enumerate(self.reads):
                if i == j:
                    continue
                if read1.overlaps(read2, overlap):
                    self.edges.add((i, j))
        if self.path_length > self.num_reads:
            raise ValueError("Requesting a path length
                        greater than number of reads.")
        self.graph_nodes, self.graph_edges = 
                        self.build_graph_repr( )
    def build_graph_repr(self):
        nodes = set( )
        edges = list( )
        # Construct path length representation of nodes/edges
        for path_step in range(1, self.path_length):
            for edge in self.edges:
                node_index1 = (path_step-1)*self.num_reads +
                        edge[0]
                node_index2 = path_step*self.num_reads +
                        edge[1]
                edges.append((node_index1, node_index2))
                nodes.add(node_index1)
                nodes.add(node_index2)
        return sorted(nodes), edges
    def __repr__(self):
        rep = ''
        for i, r in enumerate(self.reads):
```

```
              rep += '{ }: { }, '.format(i, r)
          rep = rep[:−2] + '\n' + str(self.graph_nodes) + '\n' +
                  str(self.graph_edges)
          return rep
     def get_path_length_constraints(self):
          """ Get the QUBO constraints that ensure exactly
                  path_length number of reads is used.
          """
          connections = set( )
          for read_indx in range(self.num_reads):
              this_read = [path_step * self.num_reads +
                      read_indx for path_step in
                      range(self.path_length) if path_step
                      * self.num_reads + read_indx in
                      self.graph_nodes]
              new_connections =
                      list(itertools.product(this_read,
                      this_read))
              for new_connection in new_connections:
                  if new_connection[0] != new_connection[1] and
                          new_connection[0] <
                          new_connection[1]:
                      connections.add(tuple(sorted(new_connection)))
          return sorted(connections)
     def get_read_constraints(self):
          """ Get the QUBO constraints that ensure each read is
                  used only once. """
          import itertools
          connections = set( )
          for path_step in range(self.path_length):
              this_path_step = [read_indx + path_step *
                      self.num_reads for read_indx in
                      range(self.num_reads) if read_indx +
                      path_step * self.num_reads in
                      self.graph_nodes]
              new_connections =
                      list(itertools.product(this_path_step, this_path_step))
              for new_connection in new_connections:
                  if new_connection[0] != new_connection[1] and
                          new_connection[0] <
                          new_connection[1]:
                      connections.add(tuple(sorted(new_connection)))
          return sorted(connections)
     def draw_qubo(self, solution=None):
          """ Make a visualization of the qubo. """
          points = dict( )
          # Calculate size of objects in image
          margin = 50
          dot = 25
          table_width = self.num_reads * dot + (self.num_reads +
                  1) * margin
          table_height = self.path_length * dot +
                  (self.path_length + 1) * margin
          image_width = table_width + 2 * margin
          image_height = table_height + 2 * margin
          # Make pallet
          image = Image.new('RGBA', (image_width,
                  image_height), (155, 155, 155, 255))
          draw = ImageDraw.Draw(image)
          # draw a box
          point = margin, margin
          draw.rectangle((point, (point[0] + table_width,
                  point[1] + table_height)))
          nodes_with_edges = set( )
          for edge in self.graph_edges:
              nodes_with_edges.add(edge[0])
              nodes_with_edges.add(edge[1])
          # Draw all nodes.
          for path_indx in range(self.path_length):
              for read_indx in range(self.num_reads):
                  node_index = path_indx*self.num_reads +
                          read_indx
                  x1 = point[0] + margin + read_indx * (margin +
                          dot)
                  x2 = x1 + dot
                  y1 = point[1] + margin + path_indx * (margin +
                          dot)
                  y2 = y1 + dot
                  draw.text((x1+dot/3, y1−dot),
                          '{ }'.format(node_index), 'black')
                  if node_index in nodes_with_edges:
                      draw.ellipse(((x1, y1), (x2, y2)), (0,
                              150, 155, 255))
                  else:
                      # Nodes with no incoming/outgoing edges
                          are drawn in black.
                      draw.ellipse(((x1, y1), (x2, y2)),
                              'black')
                  points[node_index] = (x1+dot/2, y2)
          # Draw logical problem edges.
          for edge in self.graph_edges:
              point_a = points[edge[0]]
              point_b = points[edge[1]]
              draw.line((point_a, (point_b[0], point_b[1]−
                      dot)), 'purple')
          # Draw first set of clique constraints (max one from
                  each column).
          constraints1 = self.get_path_length_constraints( )
          for edge in constraints1:
              point_a = points[edge[0]]
              point_b = points[edge[1]]
              draw.line((point_a, (point_b[0], point_b[1]−
                      dot)), 'green')
          # Draw second set of clique constraints (exactly one
                  from each row).
          constraints2 = self.get_read_constraints( )
          for edge in constraints2:
              point_a = points[edge[0]]
              point_b = points[edge[1]]
              draw.line((point_a, (point_b[0], point_b[1]−
                      dot)), 'blue')
          def draw_solution( ):
              possible_edges = itertools.product(solution,
                      solution)
              for edge in possible_edges:
                  if edge[0] < edge[1]:
                      if edge not in self.graph_edges:
                          continue
                      draw.line((points[edge[0]],
                              points[edge[1]]), 'black', width=3)
          # If a solution is provided, draw it in black.
          if solution is not None:
              draw_solution( )
          image.save('full_problem.png')
     def construct_qubo(self, row_strength=1, col_strength=1):
          from collections import defaultdict
          hs = [0] * self.num_reads * self.path_length
          Js = defaultdict(int)
          for edge in self.graph_edges:
              Js[edge] = −1
          constraints1 = self.get_read_constraints( )_nodes =
                  set.union(*[set(key) for key in
                          constraints1])
          for node in _nodes:
              hs[node] += −1*row_strength
          for edge in constraints1:
              Js[edge] += 2*row_strength
          constraints2 = self.get_path_length_constraints( )
          for edge in constraints2:
              Js[edge] += 2*col_strength
          return {'h': hs, 'J': Js}
     def eval(qubo, sample):
          h, J = qubo['h'], qubo['J']
          assert len(h) == len(sample)
          h_contribution = np.array(h).dot(sample)
          J_contribution = 0
          for (i, j), val in J.iteritems( ):
              J_contribution += val * sample[i] * sample[j]
          return h_contribution + J_contribution
     if __name__ == '__main__':
          import random
          seed = 2
          random.seed(seed)
          num_reads = 5
          path_length = 3
          overlap = 1
          base = '{ }{ }{ }{ }{ }'
          test_bases = [base.format(*[random.choice('1234') for _
```

```
                        in range(len(base))]) for _ in
                        range(num_reads)]
sa = SequenceAssembly(test_bases, overlap, path_length)
qubo = sa.construct_qubo(col_strength=2)
samples = lambda: itertools.product([0, 1],
                        repeat=len(sa.graph_nodes))
new_samples = list( )
for sample in samples( ):
    new_sample = np.array([0] * path_length*num_reads)
    new_sample[sa.graph_nodes] = sample
    new_samples.append(new_sample)
nodes_from_h = set(np.flatnonzero(np.array(qubo['h'])))
nodes_from_J = set( )
all_energies = list( )
for sample in new_samples:
    energy = eval(qubo, sample)
    all_energies.append(energy)
gse = min(all_energies)
real_gse = 1-2*path_length
print 'REAL GSE: { }'.format(real_gse)
invalid = None
for sample in new_samples:
    energy = eval(qubo, sample)
    if energy == real_gse:
        if sum(sample) != path_length:
            invalid = np.flatnonzero(sample)
            print 'SOLUTION { } IS
                        INVALID.'.format((invalid))
if invalid is not None:
    sa.draw_qubo(solution=invalid)
else:
    sa.draw_qubo( )
print 'GSE: { }'.format(min(all_energies))
for sample in new_samples:
    energy = eval(qubo, sample)
    if energy == gse:
        print np.flatnonzero(sample).tolist( )
```

Although specific embodiments and examples are described herein for illustrative purposes, various equivalent modifications can be made without departing from the spirit and scope of the disclosure, as will be recognized by those skilled in the relevant art. The teachings provided herein of the various embodiments can be applied to other problem-solving systems devices, and methods, not necessarily the exemplary problem-solving systems devices, and methods generally described above.

For instance, the foregoing detailed description has set forth various embodiments of the systems, devices, and/or methods via the use of block diagrams, schematics, and examples. Insofar as such block diagrams, schematics, and examples contain one or more functions and/or operations, it will be understood by those skilled in the art that each function and/or operation within such block diagrams, flowcharts, or examples can be implemented, individually and/or collectively, by a wide range of hardware, software, firmware, or virtually any combination thereof. In one embodiment, the present subject matter may be implemented via Application Specific Integrated Circuits (ASICs) or Field Programmable Gate Arrays (FPGAs).

However, those skilled in the art will recognize that the embodiments disclosed herein, in whole or in part, can be equivalently implemented in standard integrated circuits, as one or more computer programs running on one or more computers (e.g., as one or more programs running on one or more computer systems), as one or more programs running on one or more controllers (e.g., microcontrollers), as one or more programs running on one or more processors (e.g., microprocessors), as firmware, or as virtually any combination thereof, and that designing the circuitry and/or writing the code for the software and or firmware would be well within the skill of one of ordinary skill in the art in light of this disclosure.

In addition, those skilled in the art will appreciate that the mechanisms taught herein are capable of being distributed as a program product in a variety of forms, and that an illustrative embodiment applies equally regardless of the particular type of signal bearing media used to actually carry out the distribution. Examples of signal bearing media include, but are not limited to, the following: recordable type media such as floppy disks, hard disk drives, CD ROMs, digital tape, and computer memory; and transmission type media such as digital and analog communication links, for example those using TDM or IP based communication links (e.g., packet links).

The various embodiments described above can be combined to provide further embodiments.

All of the U.S. patents, U.S. patent application publications, U.S. patent applications, foreign patents, foreign patent applications and non-patent publications referred to in this specification including, but not limited to: U.S. Pat. No. 6,838,694; U.S. Patent Publication No. 2005-0082519; U.S. Patent Publication No. 2005-0273306; U.S. Patent Publication No. 2006-0147154; U.S. patent application Ser. No. 11/829,794; and U.S. Patent Application Ser. No. 62/446,157; are incorporated herein by reference, in their entirety and for all purposes. Aspects of the embodiments can be modified, if necessary, to employ systems, circuits, and concepts of the various patents, applications, and publications to provide yet further embodiments.

These and other changes can be made to the embodiments in light of the above-detailed description. In general, in the following claims, the terms used should not be construed to limit the invention to the specific embodiments disclosed in the specification and the claims, but should be construed to include all possible embodiments along with the full scope of equivalents to which such claims are entitled. Accordingly, the scope of the invention shall only be construed and defined by the scope of the appended claims.

We claim:

1. A method of problem solving via a quantum annealer, the method comprising:

for a set of a number $N_{READS}$ of nucleic acid reads r, for each nucleic acid read in the set of nucleic acid reads r, finding all other nucleic acid reads in the set of nucleic acid reads that have at least a defined number of base pairs at one end of the other nucleic acid read in common with the defined number of base pairs at one end of the nucleic acid read;

forming a problem graph having a number of rows equal to a defined sequence length $l_{SEQ}$, each row having a total number of nodes equal to the defined number of base pairs, and where for each pair of nucleic acid reads $r_{j,j}$ that have the defined number of base pairs in common, the problem graph has a respective edge that extends from a node $r_i$ in one row to a node $r_j$ in a next row in the problem graph;

for each column of the problem graph, asserting a first constraint that either one node or zero nodes in the column are in a ground state;

for each row of the problem graph, asserting a second constraint that exactly one node in the row is in the ground state;

causing the problem graph to be embedded in a hardware graph of the quantum annealer along with the first and the second constraints; and receiving a result from the quantum annealer after at least one evolution with the problem graph embedded in the hardware graph of the quantum annealer along with the first and the second constraints.

2. The method of claim 1 wherein forming a problem graph includes:

for each row of the problem graph except a last one of the rows in the problem graph, iterating over all pairs of nucleic acid reads r that have the defined number of base pairs in common, and forming an edge relationship between a node $r_i$ in one row to a node $r_j$ in a next row in the problem graph.

3. The method of claim 1 wherein finding all other nucleic acid reads in the set of nucleic acid reads that have at least a defined number of base pairs at one end of the other nucleic acid read in common with the defined number of base pairs at one end of the nucleic acid read; includes: finding all other nucleic acid reads in the set of nucleic acid reads that have at least a defined number of base pairs at a first end of the other nucleic acid read in common with the defined number of base pairs at a second end of the nucleic acid read, the second end opposite the first end.

4. The method of claim 1 wherein causing the problem graph to be embedded in a hardware graph of the quantum annealer along with the first and the second constraints includes embedding the problem graph with the first and the second constraints in the hardware graph of an analog processor.

5. The method of claim 1 wherein causing the problem graph to be embedded in a hardware graph of the quantum annealer along with the first and the second constraints includes embedding the problem graph with the first and the second constraints in the hardware graph of a quantum processor.

6. The method of claim 1 wherein the quantum annealer is a quantum processor that comprises a plurality of quantum devices spatially arranged in an interconnected topology and a plurality of coupling devices between pairs of quantum devices, and wherein causing the problem graph to be embedded in a hardware graph of the quantum annealer along with the first and the second constraints includes programming at least a portion of the plurality of quantum devices and the plurality of coupling devices to set an energy function of the quantum processor.

7. The method of claim 6, further comprising:
initializing the quantum processor to an initial state; and
evolving the quantum processor from the initial state to a final state.

8. The method of claim 7 wherein evolving the quantum processor from the initial state to a final state occurs a plurality of times via at least one of adiabatic evolution, quasi-adiabatic evolution, annealing by temperature, annealing by magnetic field, and annealing of barrier height, until a ground state energy is obtained.

9. The method of claim 1 wherein receiving a result from the quantum annealer includes receiving a result that represents an ordered sequence of nucleotides over a strand of deoxyribose nucleic acid (DNA) or ribose nucleic acid (RNA) of the defined sequence length $l_{SEQ}$.

10. A system to problem solve, the system comprising:
at least one processor circuit; and
at least one processor-readable medium that stores at least one of processor-executable instructions or data which, when executed by the at least one processor causes the at least one processor to:

form a problem graph having a number of rows equal to a defined sequence length l, each row having a total number of nodes equal to a defined number of base pairs, and where for each pair of DNA reads $r_{j,j}$ that have the defined number of base pairs in common, the problem graph has a respective edge that extends from a node $r_i$ in one row to a node $r_j$ in a next row in the problem graph;

for each column of the problem graph, assert a first constraint that either one node or zero nodes in the column are in a ground state;

for each row of the problem graph, assert a second constraint that exactly one node in the row is in the ground state;

cause the problem graph to be embedded in a hardware graph of a quantum annealer along with the first and the second constraints; and receive a result from the quantum annealer after at least one evolution with the problem graph embedded in the hardware graph of the quantum annealer along with the first and the second constraints.

11. A method of finding a path in a graph via a quantum annealer, the method comprising:

forming a problem graph having a number of rows equal to a defined sequence length $l_{SEQ}$, each row having a total number of nodes equal to a defined number of sequential values, and where for each pair of subsequences $r_{j,j}$ that have the defined number of sequential values in common, the problem graph has a respective edge that extends from a node $r_i$ in one row to a node $r_j$ in a next row in the problem graph;

for each column of the problem graph, asserting a first constraint that either one node or zero nodes in the column are in a ground state;

for each row of the problem graph, asserting a second constraint that exactly one node in the row is in the ground state;

causing the problem graph to be embedded in a hardware graph of the quantum annealer along with the first and the second constraints; and receiving a result from the quantum annealer after at least one evolution with the problem graph embedded in the hardware graph of the quantum annealer along with the first and the second constraints.

12. The method of claim 11 wherein forming a problem graph includes:

for each row of the problem graph, except a last one of the rows in the problem graph, iterating over all pairs of pair of subsequences $r_{j,j}$ that have the defined number of sequential values in common, and forming an edge relationship between a node $r_i$ in one row to a node $r_j$ in a next row in the problem graph.

13. The method of claim 11 wherein causing the problem graph to be embedded in a hardware graph of the quantum annealer along with the first and the second constraints includes embedding the problem graph with the first and the second constraints in the hardware graph of a quantum processor.

14. The method of claim 11 wherein the quantum annealer is a quantum processor that comprises a plurality of quantum devices spatially arranged in an interconnected topology and a plurality of coupling devices between pairs of quantum devices, and wherein causing the problem graph to be embedded in a hardware graph of the quantum annealer along with the first and the second constraints includes programming at least a portion of the plurality of quantum devices and the plurality of coupling devices to set an energy function of the quantum processor.

15. The method of claim 14, further comprising:
initializing the quantum processor to an initial state; and
evolving the quantum processor from the initial state to a final state.

16. The method of claim 15 wherein evolving the quantum processor from the initial state to a final state occurs a plurality of times via at least one of adiabatic evolution, quasi-adiabatic evolution, annealing by temperature, annealing by magnetic field, and annealing of barrier height, until a ground state energy is obtained.

17. The method of claim 16, further comprising:
determining whether a ground state energy was obtained at the final state of the evolution.

18. The method of claim 11 wherein forming a problem graph includes forming the problem graph having a number of rows equal to a defined sequence length $l_{SEQ}$ of a strand of nucleic acid, each row having a total number of nodes equal to a defined number of sequential base pairs, and where for each pair of subsequences $r_{j,j}$ that have the defined number of sequential base pairs in common, the problem graph has a respective edge that extends from the node $r_i$ in one row to the node $r_j$ in the next row in the problem graph.

19. The method of claim 18, further comprising:
finding all other nucleic acid reads in the set of nucleic acid reads that have at least a defined number of base pairs at one end of the other nucleic acid read in common with the defined number of base pairs at one end of the nucleic acid read.

20. The method of claim 19 wherein finding all other nucleic acid reads in the set of nucleic acid reads that have at least a defined number of base pairs at one end of the other nucleic acid read in common with the defined number of base pairs at one end of the nucleic acid read includes:
finding all other nucleic acid reads in the set of nucleic acid reads that have at least a defined number of base pairs at a first end of the other nucleic acid read in common with the defined number of base pairs at a second end of the nucleic acid read, the second end opposite the first end.

* * * * *